(12) United States Patent
Mizuno et al.

(10) Patent No.: US 11,266,349 B2
(45) Date of Patent: Mar. 8, 2022

(54) SPHYGMOMANOMETER, DEVICE, AND BLOOD PRESSURE MEASUREMENT METHOD

(71) Applicants: OMRON CORPORATION, Kyoto (JP); OMRON HEALTHCARE CO., LTD., Muko (JP)

(72) Inventors: Shinji Mizuno, Yasu (JP); Tomoyuki Nishida, Takatsuki (JP); Hirokazu Tanaka, Otsu (JP); Noboru Kohara, Okayama (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 210 days.

(21) Appl. No.: 16/504,476

(22) Filed: Jul. 8, 2019

(65) Prior Publication Data
US 2019/0328324 A1  Oct. 31, 2019

Related U.S. Application Data

(63) Continuation of application No. PCT/JP2017/046553, filed on Dec. 26, 2017.

(30) Foreign Application Priority Data

Mar. 7, 2017 (JP) .............................. JP2017-042493

(51) Int. Cl.
*A61B 5/00* (2006.01)
*A61B 5/021* (2006.01)
*A61B 5/022* (2006.01)

(52) U.S. Cl.
CPC .......... *A61B 5/681* (2013.01); *A61B 5/02141* (2013.01); *A61B 5/02233* (2013.01); *A61B 2562/0247* (2013.01)

(58) Field of Classification Search
CPC .. A61B 5/681; A61B 5/02141; A61B 5/02233
(Continued)

(56) References Cited

U.S. PATENT DOCUMENTS

| 2003/0056598 | A1 | 3/2003 | Kimura et al. |
| 2005/0015015 | A1* | 1/2005 | Mizukoshi ......... A61B 5/02233 600/499 |

(Continued)

FOREIGN PATENT DOCUMENTS

| JP | H10-038734 A | 2/1998 |
| JP | 2003-004567 A | 1/2003 |

(Continued)

OTHER PUBLICATIONS

Mar. 20, 2018 International Search Report issued in International Patent Application No. PCT/JP2017/046553.

*Primary Examiner* — Daniel L Cerioni
*Assistant Examiner* — Deirdre M Willgohs
(74) *Attorney, Agent, or Firm* — Oliff PLC

(57) ABSTRACT

A sphygmomanometer includes a cuff and a main body. The main body is equipped with a substrate, a pump and a pressure sensor that are attached to one surface of the substrate, and a plate-shaped member opposed to an other surface of the substrate on an opposite side of the one surface of the substrate. The substrate includes a first through-hole and a second through-hole. The other surface of the substrate and an opposing surface of the plate-shaped member opposed to the other surface constitute the planar direction passage extending in a planar direction along the other surface of the substrate. The planar direction passage communicates with a fluid bag of the cuff. The sphygmomanometer further includes a pressurization controller and a blood pressure calculator. The pressurization controller controls pressing the measured site through the planar direction (Continued)

passage. The blood pressure calculator calculates a blood pressure.

18 Claims, 23 Drawing Sheets

(58) Field of Classification Search
USPC .......................................................... 600/490
See application file for complete search history.

(56) References Cited

U.S. PATENT DOCUMENTS

| | | | |
|---|---|---|---|
| 2006/0116588 A1* | 6/2006 | Archibald | A61B 5/02233 600/494 |
| 2011/0144507 A1* | 6/2011 | Sano | A61B 5/02233 600/499 |
| 2012/0253210 A1* | 10/2012 | Uesaka | A61B 5/684 600/499 |
| 2015/0025400 A1 | 1/2015 | Nishioka et al. | |
| 2015/0182138 A1* | 7/2015 | Yoshino | A61B 5/02233 600/499 |

FOREIGN PATENT DOCUMENTS

| | | |
|---|---|---|
| JP | 2005-172432 A | 6/2005 |
| JP | 2007-278236 A | 10/2007 |
| JP | 2009-203979 A | 9/2009 |
| JP | 2010-088513 A | 4/2010 |
| JP | 2012-217684 A | 11/2012 |
| JP | 2013-220187 A | 10/2013 |

* cited by examiner

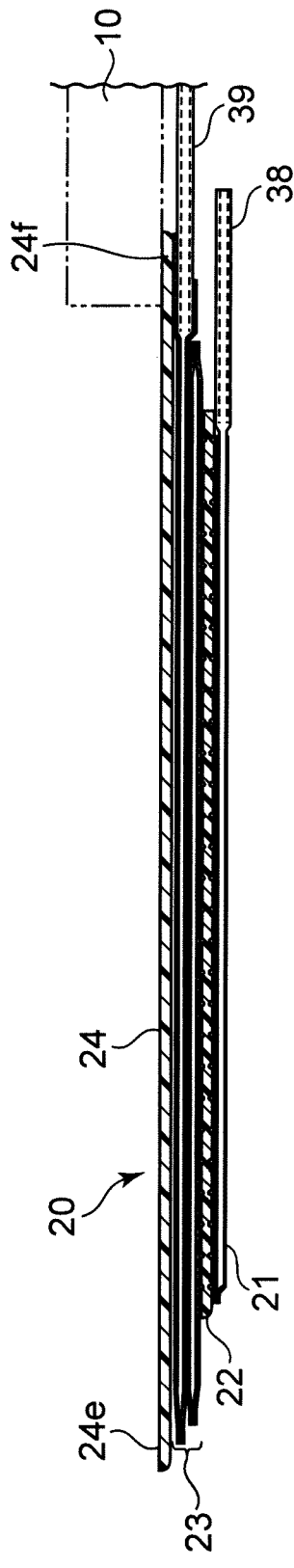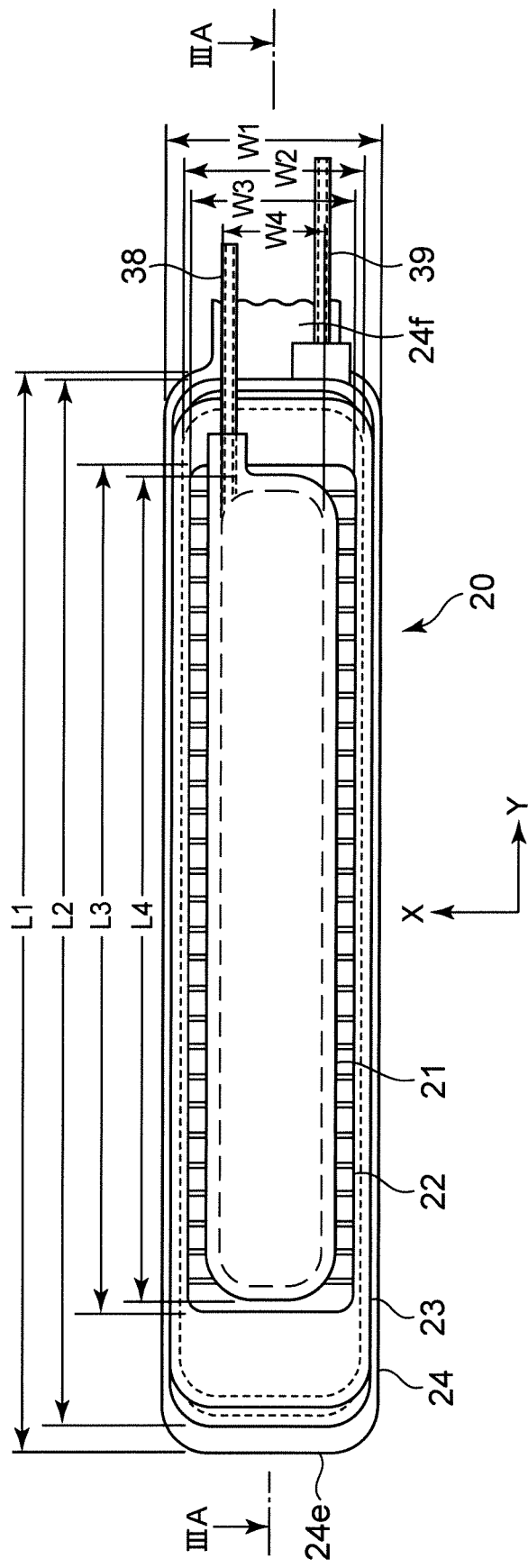

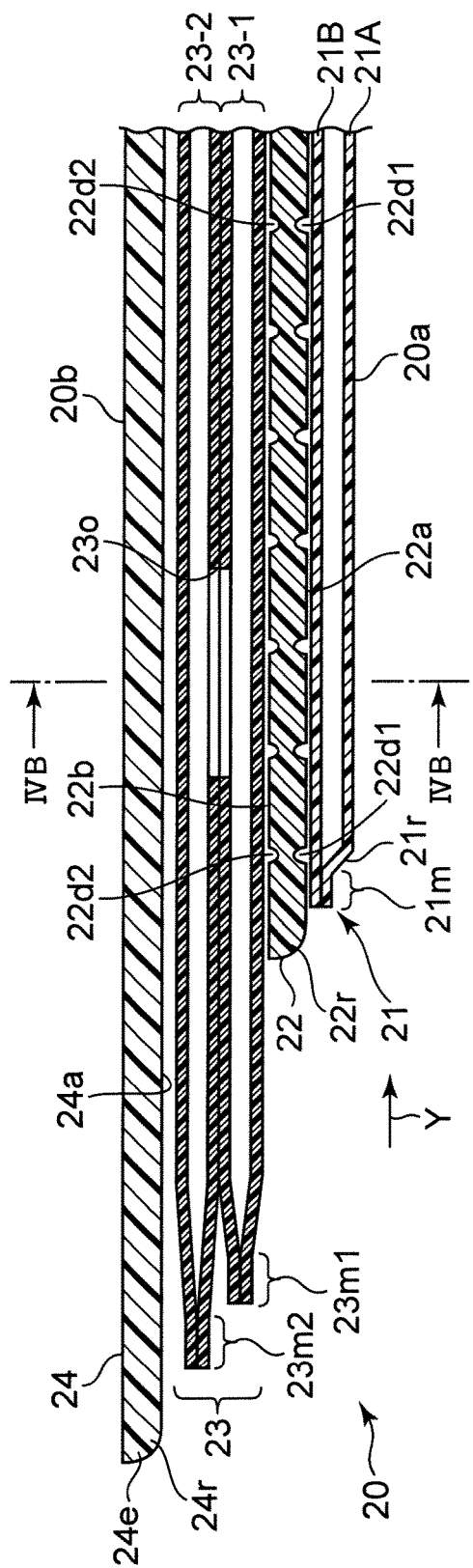
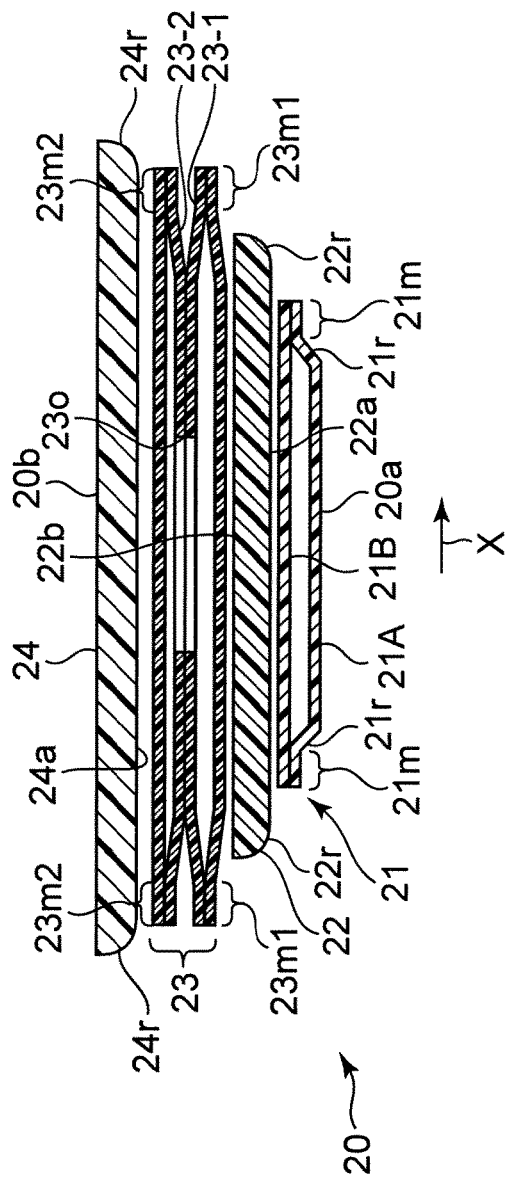

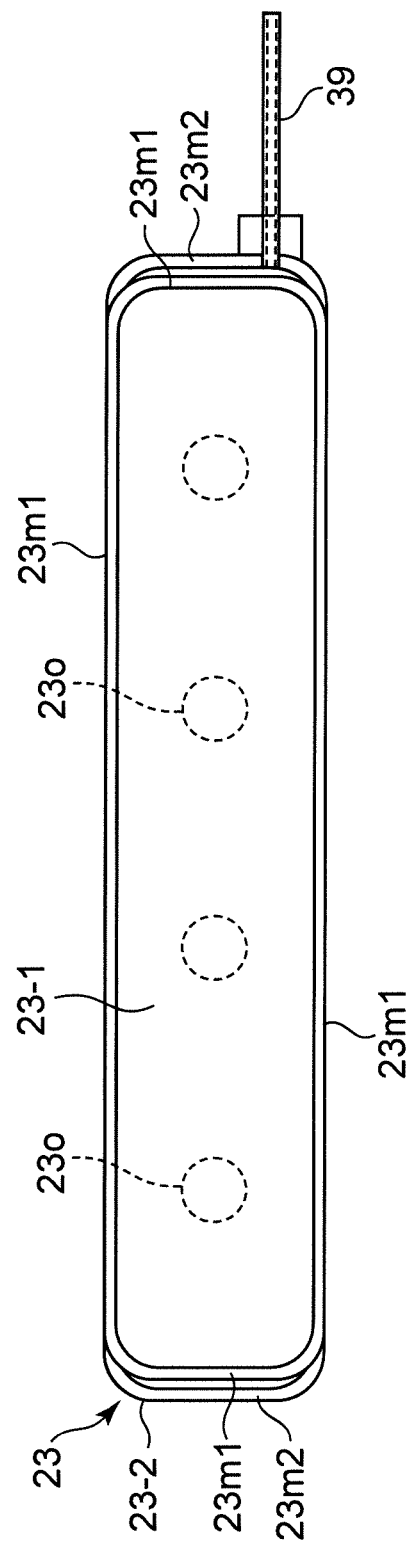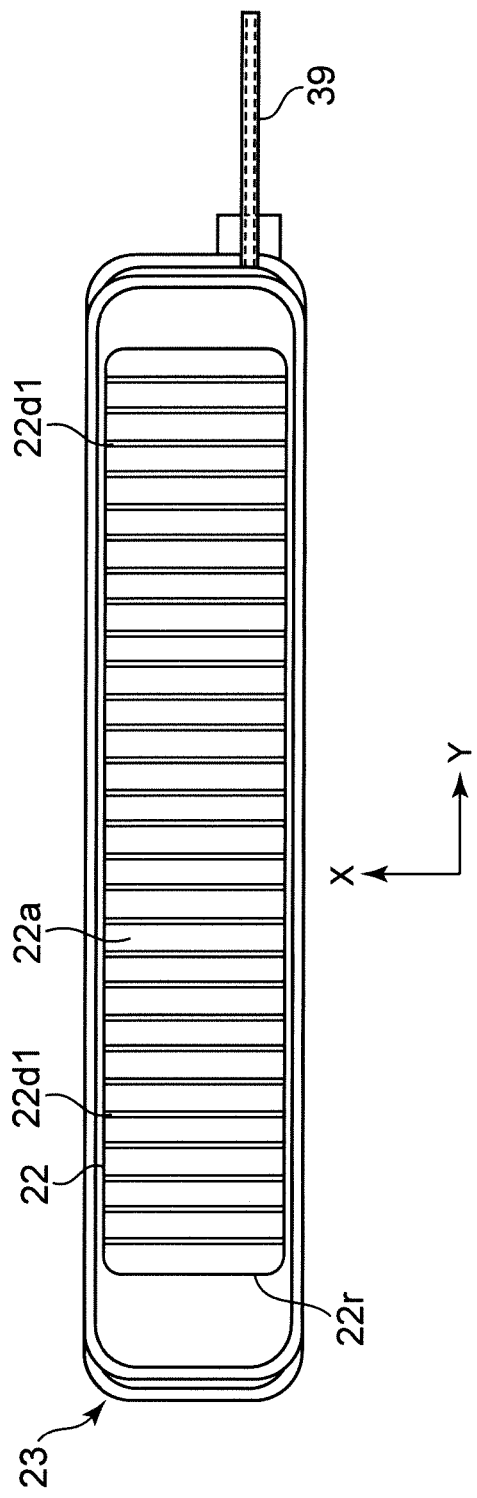

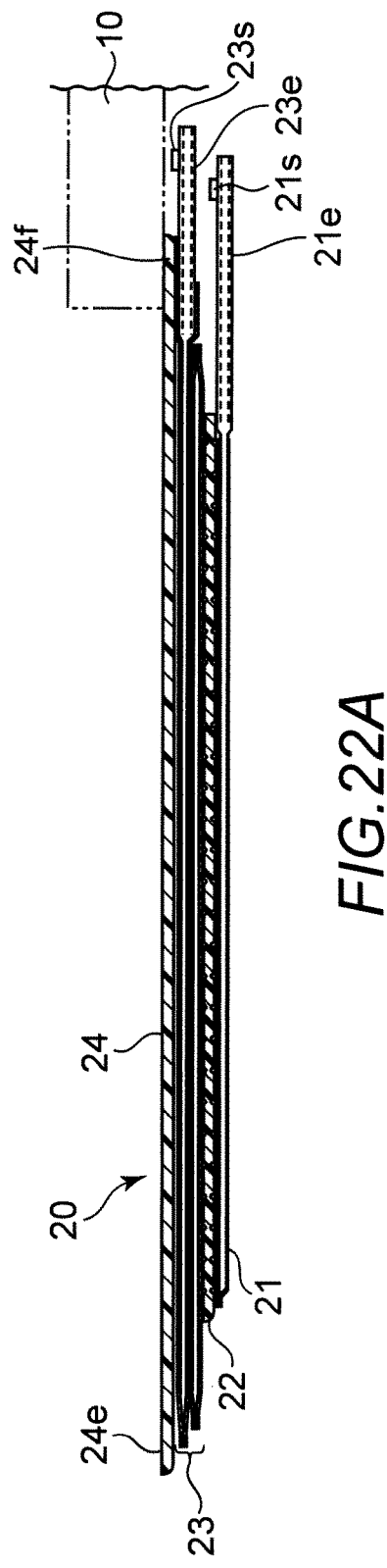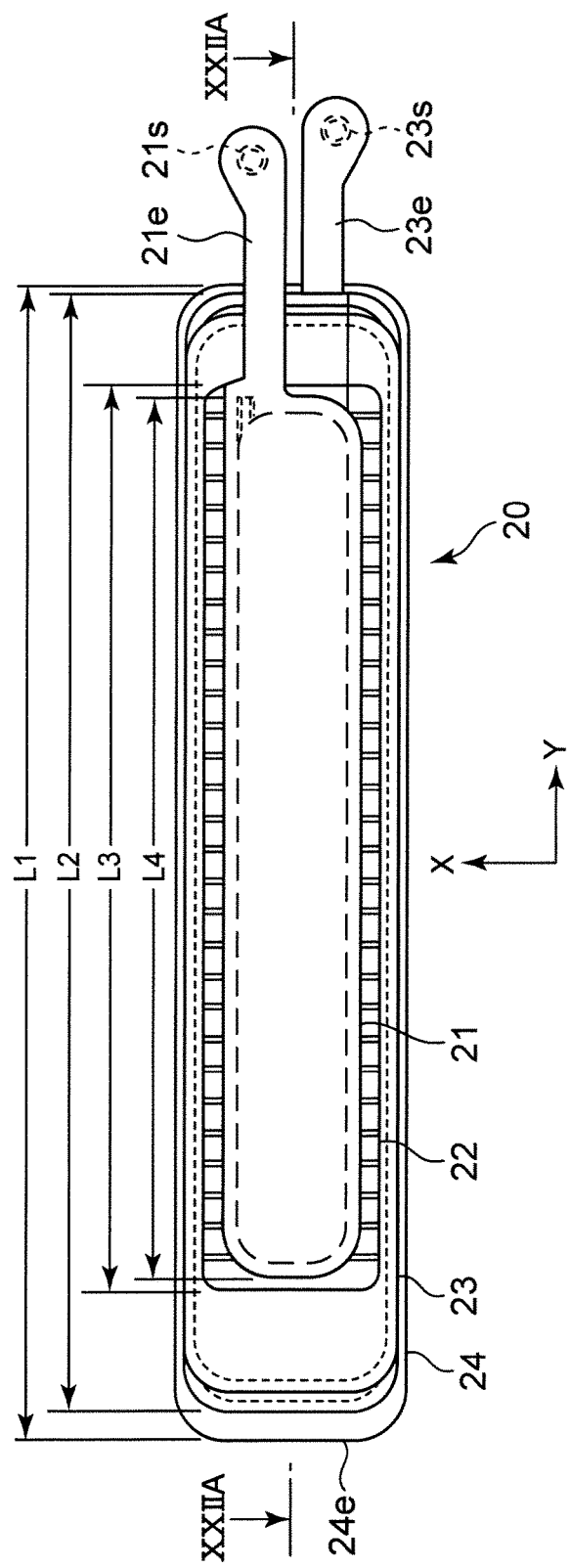

SPHYGMOMANOMETER, DEVICE, AND BLOOD PRESSURE MEASUREMENT METHOD

CROSS-REFERENCE TO RELATED APPLICATIONS

The present application is a continuation application of International Application No. PCT/JP2017/046553, filed Dec. 26, 2017, which claims priority to Japanese Patent Application No. 2017-042493, filed Mar. 7, 2017. The contents of these applications are incorporated herein by reference in their entirety.

BACKGROUND OF THE INVENTION

Field of the Invention

The present invention relates to a sphygmomanometer, device, and a blood pressure measurement method.

Discussion of the Background

Conventionally, as this kind of sphygmomanometer, for example, as disclosed in Japanese Patent Application Publication No. 2013-220187, the cuff that includes a fluid bag and is worn while binding the measured site and the main body equipped with the pump and the pressure sensor are disposed while overlapping each other in a thickness direction. In this sphygmomanometer, the pump and the fluid bag are connected through a first fluid path (air piping) extending straight in the thickness direction, and the pressure sensor and the fluid bag are connected through a second fluid path (air piping) extending straight in the thickness direction. Consequently, miniaturization in a planar direction (a direction in which a plane perpendicular to the thickness direction extends) of the product is achieved.

SUMMARY OF THE INVENTION

According to a first aspect of the present disclosure, a sphygmomanometer includes
a cuff to be worn while binding a measured site, and
a main body, wherein
the main body is equipped with a substrate, a pump and a pressure sensor that are attached to one surface of the substrate, and a plate-shaped member opposed to an other surface of the substrate on an opposite side of the one surface of the substrate,
the substrate includes a first through-hole at a portion corresponding to a fluid discharge port of the pump, and a second through-hole at a portion corresponding to a fluid intake port of the pressure sensor,
the other surface of the substrate and an opposing surface of the plate-shaped member opposed to the other surface constitute the planar direction passage extending in a planar direction along the other surface of the substrate,
the planar direction passage communicates with a fluid bag of the cuff, and
the sphygmomanometer further includes
a pressurization controller to control pressing the measured site with supplying fluid from the pump to the fluid bag through the first through-hole and the planar direction passage, and
a blood pressure calculator to calculate a blood pressure based on an output of the pressure sensor while the fluid is introduced from the fluid bag to the pressure sensor through the planar direction passage and the second through-hole.

According to a second aspect of the present disclosure, a device includes
a cuff to be worn while binding a measured site, and
a main body including a blood pressure measurement element, wherein
the main body is equipped with a substrate, a pump and a pressure sensor that are attached to one surface of the substrate as the blood pressure measurement element, and a plate-shaped member opposed to the other surface of the substrate on an opposite side of the one surface of the substrate,
the substrate includes the first through-hole at a portion corresponding to a fluid discharge port of the pump, and the second through-hole at a portion corresponding to a fluid intake port of the pressure sensor,
the other surface of the substrate and an opposing surface of the plate-shaped member opposed to the other surface constitute the planar direction passage extending in a planar direction along the other surface of the substrate,
the planar direction passage communicates with a fluid bag of the cuff, and
the device further includes
a pressurization controller to control pressing the measured site with supplying fluid from the pump to the fluid bag through the first through-hole and the planar direction passage, and
a blood pressure calculator to calculate a blood pressure based on an output of the pressure sensor while the fluid is introduced from the fluid bag to the pressure sensor through the planar direction passage and the second through-hole.

According to a third aspect of the present disclosure, a blood pressure measurement method for measuring a blood pressure of a measured site using a sphygmomanometer including a cuff that is worn while binding the measured site and a main body which is equipped with a substrate, a pump and a pressure sensor that are attached to one surface of the substrate, and a plate-shaped member opposed to an other surface of the substrate on an opposite side of the one surface of the substrate, the substrate including a first through-hole at a portion corresponding to a fluid discharge port of the pump and a second through-hole at a portion corresponding to a fluid intake port of the pressure sensor, the other surface of the substrate and an opposing surface of the plate-shaped member opposed to the other surface constituting a planar direction passage extending in a planar direction along the other surface of the substrate, and the planar direction passage communicating with a fluid bag of the cuff, the blood pressure measurement method includes
while the cuff is worn on the measured site,
controlling pressing the measured site with supplying fluid from the pump to the fluid bag through the first through-hole and the planar direction passage, and
calculating a blood pressure based on an output of the pressure sensor while the fluid is introduced from the fluid bag to the pressure sensor through the planar direction passage and the second through-hole.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 3A is a view illustrating a section taken along a line IIIA-IIIA in FIG. 3B.

FIG. 3B is a view illustrating a planar layout when a cuff structure in FIG. 2 is in an expanded state while an inner circumferential surface is set to a forefront.

FIG. 4A is an enlarged view illustrating a vicinity of a leading end of the cuff structure in FIG. 3B.

FIG. 4B is a view illustrating a section taken along a line IVB-IVB in FIG. 4A.

FIG. 5A is a view illustrating a planar layout of a pressing cuff included in the cuff structure.

FIG. 5B is a view illustrating a planar layout of a backboard included in the cuff structure while the pressing cuff is set to a background.

FIG. 22A is a view illustrating a section taken along a line XXIIA-XXIIA in FIG. 22B.

FIG. 22B is a view illustrating a planar layout of a cuff structure of the first modification when the cuff structure is in the expanded state while the inner circumferential surface of the cuff structure is set to the forefront.

DESCRIPTION OF THE EMBODIMENTS

Figure 1:
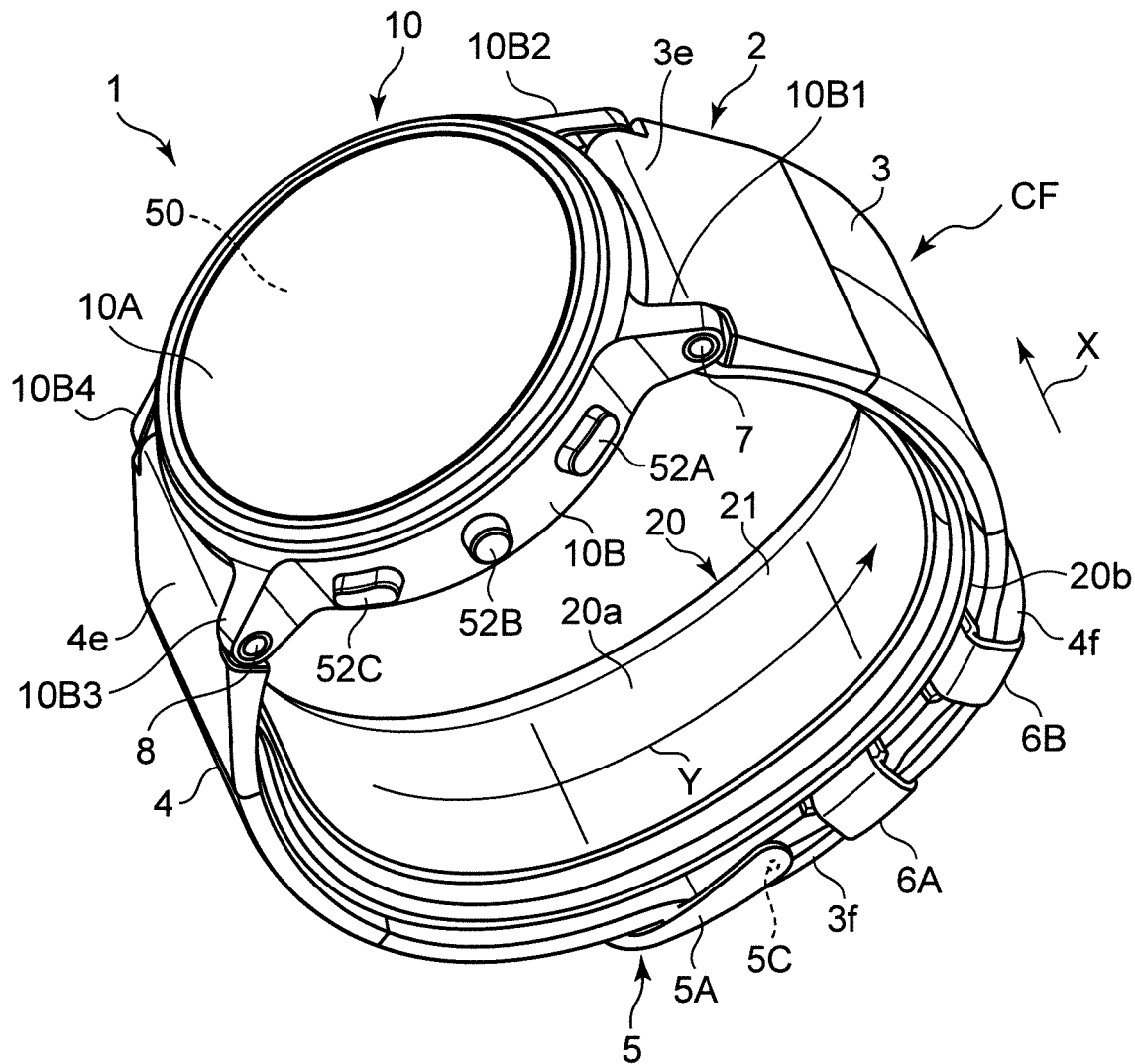
FIG. 1 is a view illustrating an external appearance of a sphygmomanometer according to an embodiment of the present invention when the sphygmomanometer is obliquely viewed with a belt fastened.

The embodiments will now be described with reference to the accompanying drawings, wherein like reference numerals designate corresponding or identical elements throughout the various drawings.

Hereinafter, embodiments of the present invention will be described in detail with reference to the drawings.

(Configuration of Sphygmomanometer)

Figure 2:
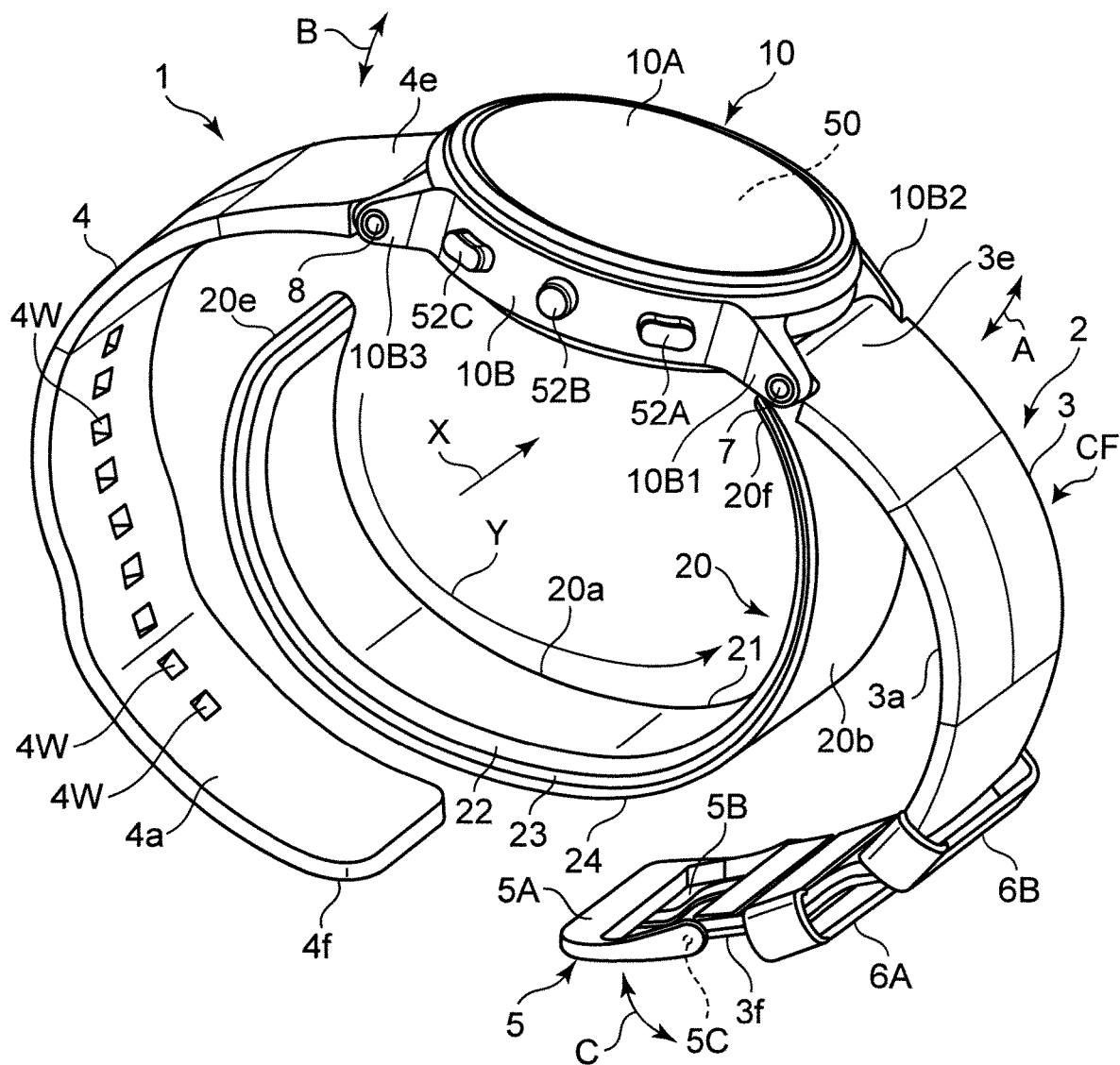
FIG. 2 is a view illustrating the external appearance of the sphygmomanometer when the sphygmomanometer is obliquely viewed with the belt opened.

FIG. 1 illustrates an external appearance of a sphygmomanometer according to an embodiment of the present invention (the whole is indicated by the reference numeral 1) when the sphygmomanometer is obliquely viewed with a belt 2 fastened. FIG. 2 illustrates the external appearance of the sphygmomanometer 1 when the sphygmomanometer 1 is obliquely viewed with the belt 2 unfastened.

Figure 14A:
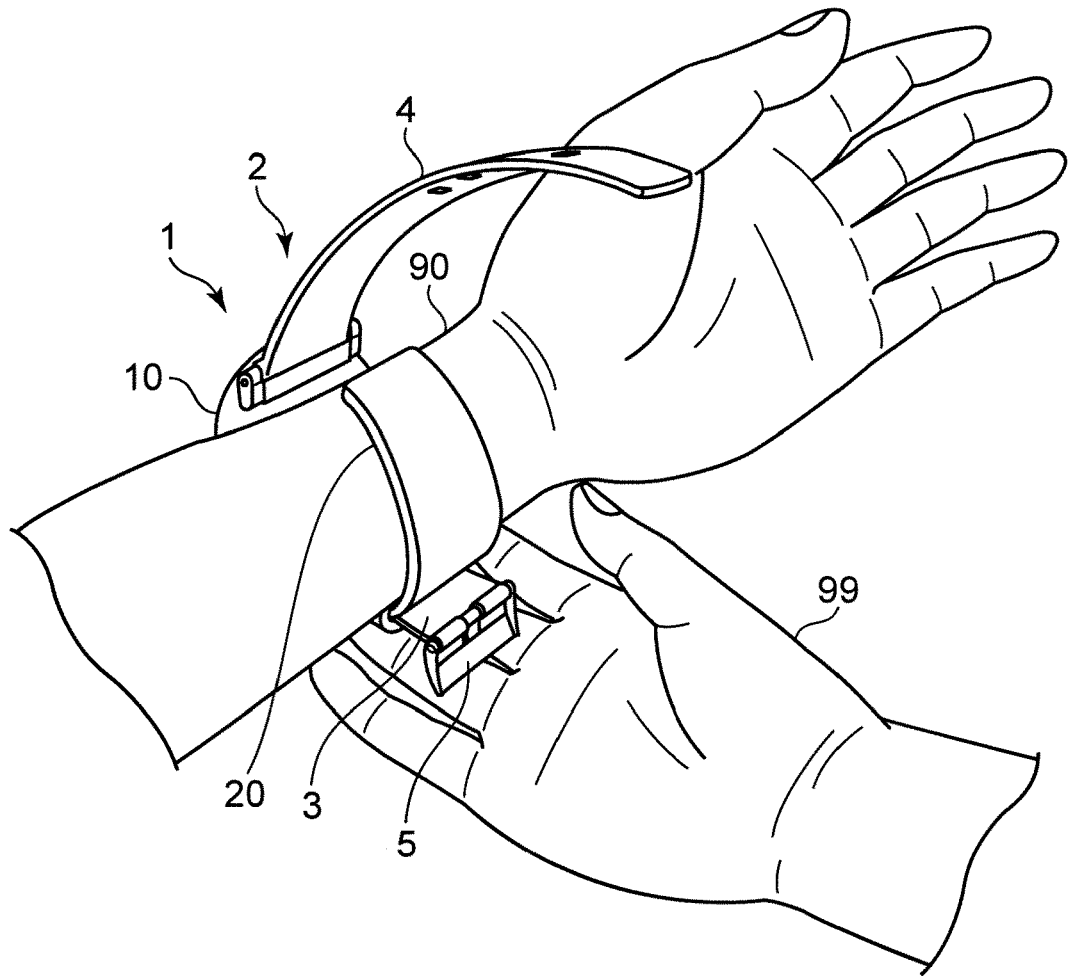
FIG. 14A is a perspective view illustrating a state in which the user wears the cuff structure on the left wrist using a right hand.
Figure 14B:
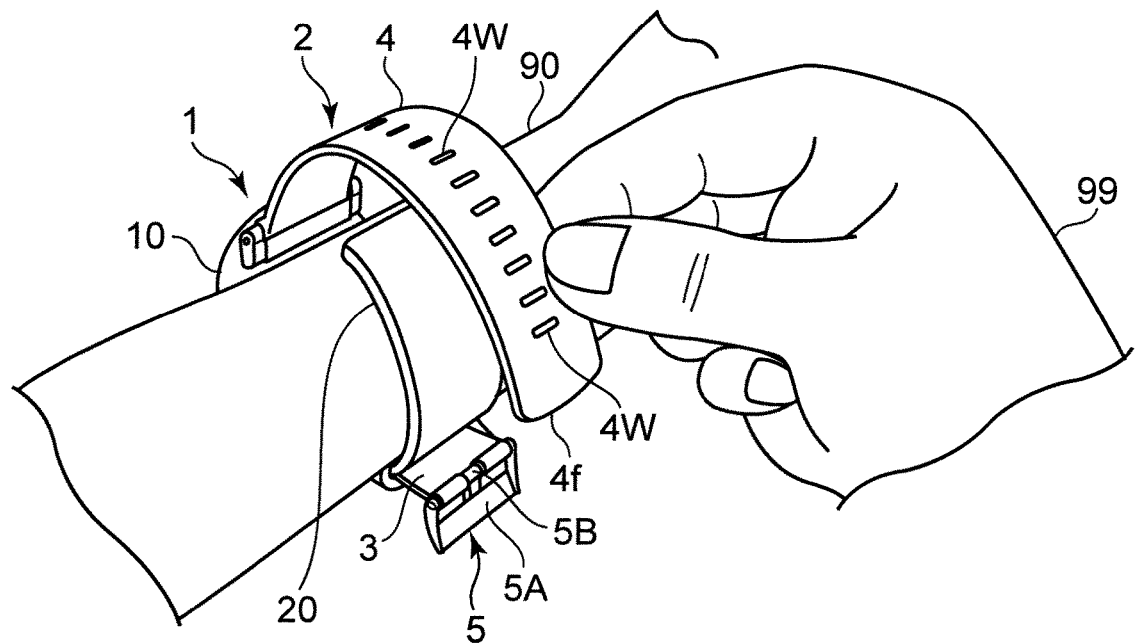
FIG. 14B is a perspective view illustrating a state when the user uses a right hand to collectively bind the left wrist and the cuff structure with a belt.
Figure 14C:
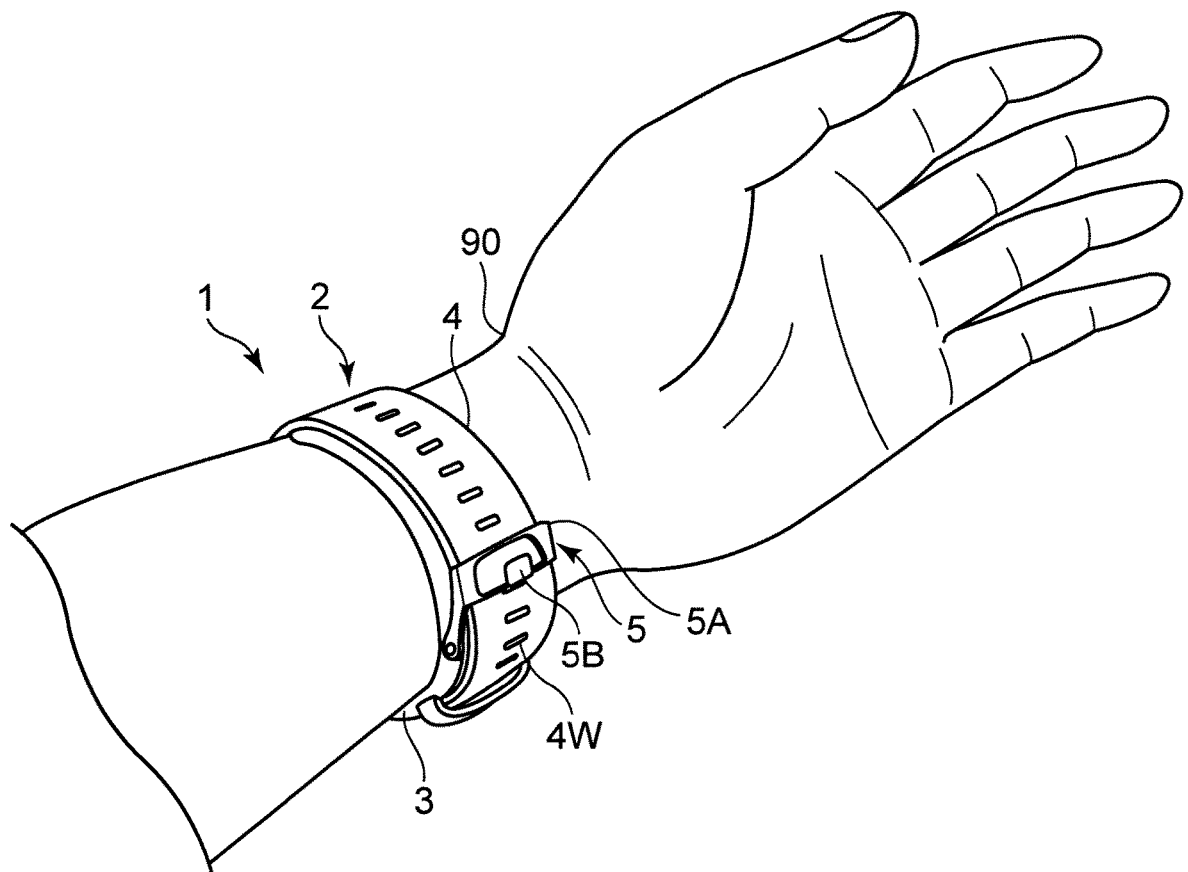
FIG. 14C is a perspective view illustrating a state in which the sphygmomanometer is worn on the left wrist of the user.

As illustrated in FIGS. 1 and 2, the sphygmomanometer 1 roughly includes a main body 10, the belt 2 that extends from the main body 10 to be worn while binding a measured site (in this example, as illustrated in FIG. 14C, a left wrist 90 is intended to be measured as the measured site), and a belt-shaped cuff structure 20 in which one end 20f is attached to the main body 10. In this example, a dimension in a width direction X of the belt 2 is set to 29 mm. In this example, a thickness of the belt 2 is set to 2 mm. In this example, the belt 2 and the cuff structure 20 constitute a cuff CF.

In this example, the main body 10 includes a case 10B having a substantially short cylindrical shape, a circular glass 10A attached to an upper portion (in FIGS. 1 and 2) of the case 10B, and a back lid 10C (see FIG. 6) attached to a lower portion of the case 10B. Pairs of protruding lugs 10B1, 10B2 and 10B3, 10B4 (in FIGS. 1 and 2) on the left and right sides are integrally provided on side surfaces of the case 10B in order to attach the belt 2. In this example, the case 10B and the back lid 10C are made of stainless steel.

A display 50 constituting a display screen is provided in a glass 10A of the upper portion of case 10B. On the side surface of the front side (in FIGS. 1 and 2) of the main body 10, a measurement switch 52A that gives an instruction to start or stop blood pressure measurement, a home switch 52B that returns the display screen of the display 50 to a predetermined home screen, and a recording call switch 52C that instructs the display 50 to display a measurement record such as a blood pressure and an activity mass in the past are provided (these switches are collectively referred to as the operation unit 52). Also, inside the main body 10, a blood pressure measurement element including a pump 30 is mounted (to be described in detail later). In this example, the sphygmomanometer 1 includes the functions of an activity meter and a pulse monitor. That is, the sphygmomanometer 1 is configured as a multifunctional device having an aspect of a wristwatch type wearable device. The main body 10 is small and thin so as not to interfere with the daily activities of a user. In this example, the thickness of the main body 10 is set in a range of 10 mm to 12 mm.

As can clearly be seen from FIG. 2, the belt 2 has a belt-shaped first belt 3 extending from the main body 10 to one side (right side in FIG. 2) in one direction and a belt-shaped second belt 4 extending from the main body 10 to the other side (left side in FIG. 2) in one direction. A root 3e of the first belt 3 on the side closer to the main body 10 is attached to the lugs 10B1, 10B2 of the main body 10 so as to be turnable as illustrated by a two-way arrow A about a connecting rod 7 (known spring rod) extending in a width direction X of the belt. Similarly, a root 4e of the second belt 4 on the side closer to the main body 10 is attached to the lugs 10B3, 10B4 of the main body 10 so as to be turnable as illustrated by a two-way arrow B about a connecting rod 8 (known spring rod) extending in the width direction X of the belt.

A tail lock 5 is attached to a leading end 3f of the first belt 3 on the side farther from the main body 10. The tail lock 5 is a known type, and includes a frame-shaped body 5A having a substantial U-shape, a prong 5B, and a connecting rod 5C extending in the width direction X of the belt. The frame-shaped body 5A and the prong 5B are attached to the leading end 3f of the first belt 3 on the side farther from the main body 10 so as to be turnable as indicated by a two-way arrow C about the connecting rod 5C. Between the leading end 3f and the root 3e of the first belt 3, ring-shaped belt holders 6A, 6B are integrally provided at a predetermined position with respect to a longitudinal direction (corresponding to a circumferential direction Y of the left wrist 90) of the first belt 3. An inner circumferential surface 3a of the first belt 3 does not protrude toward the inner circumferential side at places of the belt holders 6A, 6B, but is formed substantially flat (locally although it curved as a whole). Consequently, the belt 2 uniformly binds and restrains the outer circumferential side of the cuff structure 20.

A plurality of small holes 4w, 4w, . . . are made between the root 4e and the leading end 4f on the side farther from the main body 10 in the second belt 4 while being pierced in a thickness direction of the second belt 4. When the first belt 3 and the second belt 4 are fastened, a portion connected to the leading end 4f of the second belt 4 is passed through the frame-shaped body 5A of the tail lock 5, and the prong 5B of the tail lock 5 is inserted into one of the plurality of small holes 4w, 4w, . . . of the second belt 4. Consequently, the first belt 3 and the second belt 4 are fastened as illustrated in FIG. 1.

In this example, the first belt 3 and the second belt 4 constituting the belt 2 are made of a plastic material exhibiting flexibility in the thickness direction and substantial non-stretchability in the longitudinal direction (corresponding to the circumferential direction Y of the left wrist 90). Consequently, the belt 2 can easily bind and restrain the outer circumferential side of the cuff structure 20 during the wear, and assist compression of the left wrist 90 during the blood pressure measurement (to be described later). The first belt 3 and the second belt 4 may be made of a leather material. Although the frame-shaped body 5A and the prong 5B that constitute the tail lock 5 are made of a metal material in this example, the frame-shaped body 5A and the prong 5B may be made of a plastic material.

As illustrated in FIG. 2, the cuff structure 20 includes a curler 24 disposed at an outermost circumference, a pressing cuff 23 that is a fluid bag disposed along an inner circumferential surface of the curler 24, a backboard 22 that is a reinforcing plate disposed along the inner circumferential surface of the pressing cuff 23, and a sensing cuff 21 that is a fluid bag disposed along the inner circumferential surface of the backboard 22.

FIG. 3B illustrates a planar layout when the cuff structure 20 in FIG. 2 is in the expanded state while an inner circumferential surface 20a of the cuff structure 20 is set to a forefront. FIG. 3A illustrates a section taken along a line IIIA-IIIA in FIG. 3B. FIG. 4A is an enlarged view illustrating a vicinity of a leading end of the cuff structure 20 in FIG. 3B. FIG. 4B illustrates a section taken along a line IVB-IVB in FIG. 4A. FIG. 5A illustrates a planar layout of the pressing cuff 23. FIG. 5B illustrates a planar layout of the backboard 22 while the pressing cuff 23 is set to a background.

As illustrated in FIGS. 3A and 3B, each of the curler 24, the pressing cuff 23, the backboard 22, and the sensing cuff 21 has an elongated belt shape in one direction (Y direction). In this example, the dimension in the width direction X of the curler 24 is set to W1=28 mm, the dimension (excluding the edges on both welded sides) in the width direction X of the pressing cuff 23 is set to W2=25 mm, the dimension in the width direction X of the backboard 22 is set to W3=23 mm, and the dimension (excluding the edges on both welded sides) in the width direction X of the sensing cuff 21 is set to W4=15 mm. The dimension (excluding the root 24f attached to the main body 10) in the longitudinal direction Y of the curler 24 is set to L1=148 mm, the dimension in the longitudinal direction Y of the pressing cuff 23 is set to L2=140 mm, and the dimension in the longitudinal direction Y of the backboard 22 is set to L3=114 mm, and the dimension in the longitudinal direction Y of the sensing cuff 21 is set to L4=110 mm.

As can be seen from FIGS. 4A and 4B, the sensing cuff 21 includes a first sheet 21A on the side that is in contact with the left wrist 90 and a second sheet 21B opposite to the first sheet 21A, the circumferential edges 21m of the first and second sheets 21A, 21B come close contact with each other by welding, and the sensing cuff 21 is formed into a bag shape. In this example, as illustrated in FIG. 4B, sags 21r, 21r extending along the longitudinal direction Y of the sensing cuff 21 in a natural state are provided at places continuous with the edges 21m, 21m on both sides with respect to the width direction X of the sensing cuff 21. As illustrated in FIG. 4A, the sag 21r extending along the width direction X of the sensing cuff 21 in the natural state is provided at the places continuous with the edges 21m on both sides (only the edge 21m on the leading end side is illustrated in FIG. 4A) with respect to the longitudinal direction Y of the sensing cuff 21 in the first sheet 21A. For example, the sag 21r can be formed by a known method when the circumferential edges 21m of the first and second sheets 21A, 21B are welded and brought into close contact with each other. As can be seen from FIGS. 3A and 3B, a flexible tube 38 that supplies a pressure transmitting fluid (in this example, air) to the sensing cuff 21 or discharges the pressure transmitting fluid from the sensing cuff 21 is provided at an end of the root side (+Y side) with respect to the longitudinal direction Y of the sensing cuff 21. In this example the first and second sheets 21A, 21B is made of a stretchable polyurethane sheet (thickness t=0.15 mm). The inner circumferential surface 20a of the cuff structure 20 is constructed with the first sheet 21A of the sensing cuff 21.

As seen from FIGS. 4A and 4B, the pressing cuff 23 includes two fluid bags 23-1, 23-2 stacked in the thickness direction. The two stretchable polyurethane sheets (thickness t=0.15 mm) are opposed to each other, and the circumferential edges 23m1, 23m2 of the polyurethane sheets are welded to form the fluid bags 23-1, 23-2. As illustrated in FIG. 5A, the dimension in the longitudinal direction Y of the fluid bag 23-1 on the inner circumferential side is set slightly smaller than the dimension (L2) in the longitudinal direction Y of the fluid bag 23-2 on the outer circumferential side. A flexible tube 39 that supplies the pressure transmitting fluid (in this example, air) to the pressing cuff 23 or discharges the pressure transmitting fluid from the pressing cuff 23 is provided at the end of the root side (+Y side) with respect to the longitudinal direction Y of the fluid bag 23-2 on the outer circumferential side. A plurality (in this example, four) of through-holes 23o, 23o, . . . are made between the fluid bag 23-1 on the inner circumferential side and the fluid bag 23-2 on the outer circumferential side adjacent to the fluid bag 23-1. Consequently, a pressurization fluid (in this example, air) can flow between the two fluid bags 23-1, 23-2 through the through-holes 23o, 23o, . . . . Consequently, when the pressing cuff 23 receives the supply of the pressurization fluid from the side of the main body 10 through the flexible tube 39 in the worn state, the two stacked fluid bags 23-1, 23-2 are inflated to press the left wrist 90 as a whole.

Figure 13:
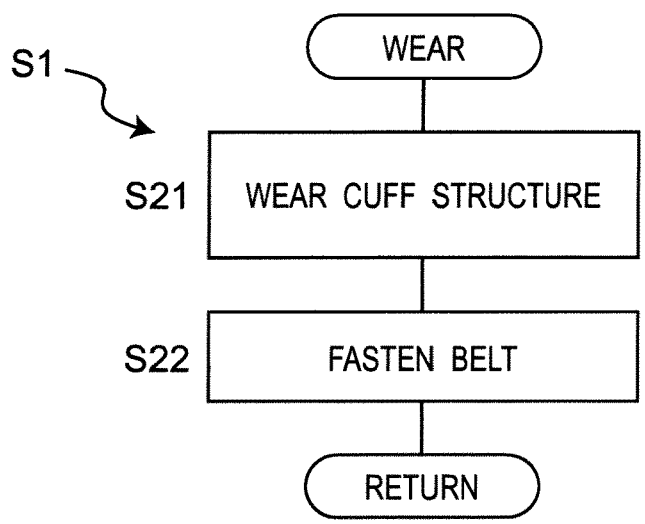
FIG. 13 is a flowchart illustrating processing in which the user wears the sphygmomanometer on a left wrist.

In this example, the backboard 22 is made of a plate-shaped resin (in this example, polypropylene) having a thickness of about 1 mm. As can be seen from FIGS. 3A and 3B, the backboard 22 extends into a belt shape beyond a length of the sensing cuff 21 in the longitudinal direction Y (corresponding to the circumferential direction of the left wrist 90). Thus, the backboard 22 acts as a reinforcing plate, and can transmit pressing force from the pressing cuff 23 to the entire region in the longitudinal direction Y (corresponding to the circumferential direction of the left wrist 90) of the sensing cuff 21. As can be seen from FIGS. 4A and 5B, in the inner circumferential surface 22a and the outer circumferential surface 22b of the backboard 22, a plurality of V-shape or U-shape grooves 22d1, 22d2 in a section extending in the width direction X are formed in parallel with each other while separated from each other in the longitudinal direction Y. In this example, the grooves 22d1, 22d2 are provided at the same position while corresponding to each other between the inner circumferential surface 22a and the outer circumferential surface 22b of the backboard 22. Consequently, the backboard 22 becomes thinner at the places of the grooves 22d1, 22d2 as compared with other places, and is easy bend. Thus, when the user collectively binds the left wrist 90 and the cuff structure 20 with the belt 2 during the wear (step S22 in FIG. 13), the backboard 22 does not prevent the cuff structure 20 from being curved along the circumferential direction Y of the left wrist 90.

Figure 7:
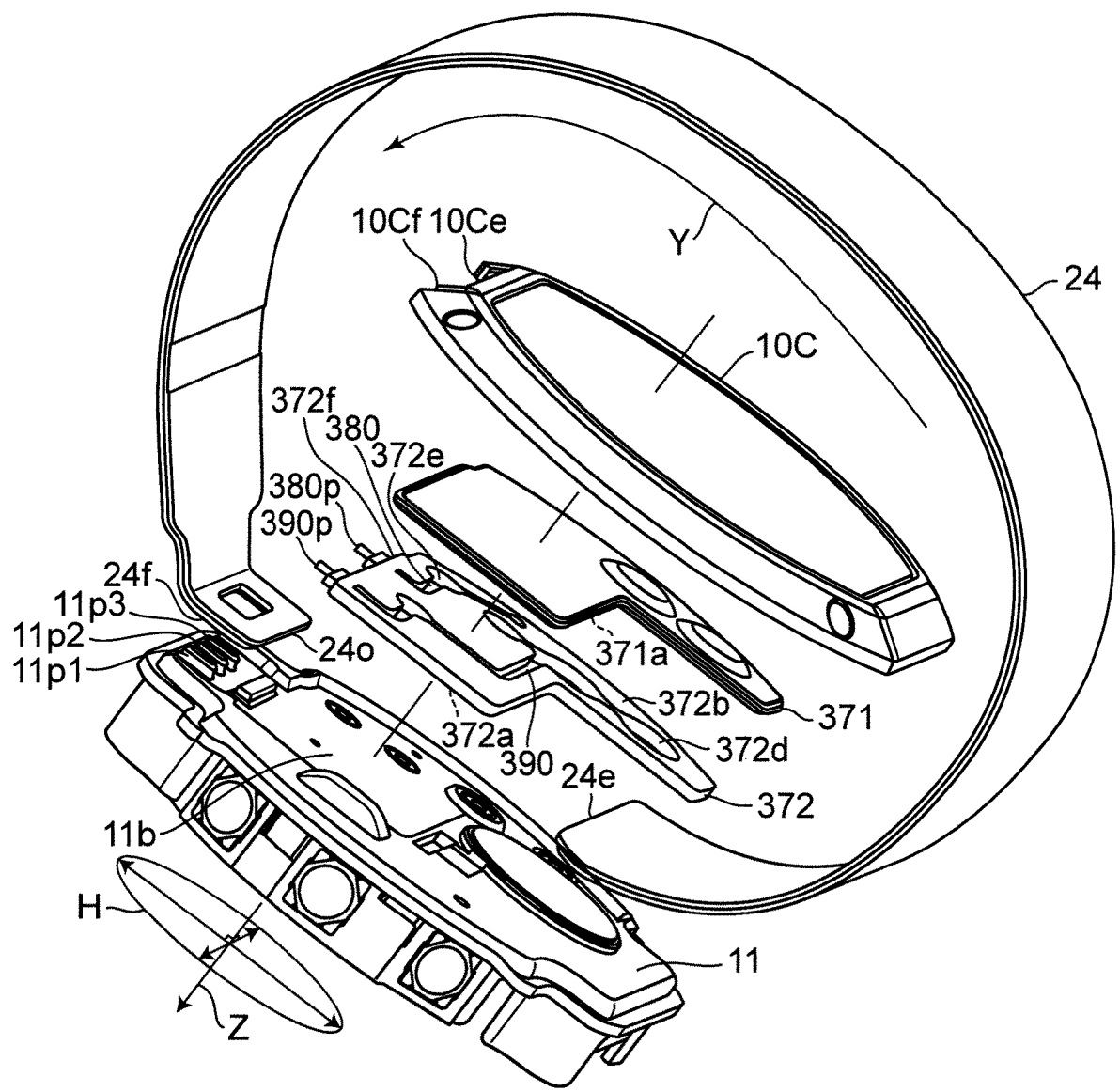
FIG. 7 is a view illustrating the back side of the main body including a curler included in the cuff structure in a disassembled state in which a back lid is removed.

In this example, the curler 24 is made of a resin plate (in this example, polypropylene) having the thickness of about 1 mm and a certain degree of flexibility and hardness. As can be seen from FIGS. 3A and 3B, in the expanded state, the curler 24 extends into the belt shape beyond the length of the pressing cuff 23 in the longitudinal direction Y (corresponding to the circumferential direction of the left wrist 90). As illustrated in FIG. 7, in the natural state, the curler 24 has a curved shape along the circumferential direction Y surrounding the left wrist 90. Consequently, the shape in the natural state of the cuff structure 20 is kept curved along the circumferential direction Y of the left wrist 90 as illustrated in FIG. 2.

Rounds 22r, 24r curved in a direction going away from the measured site (in this example, the left wrist 90) are formed at the circumferential edge of the inner circumferential surface 22a of the backboard 22 and the circumferential edge of the inner circumferential surface 24a of the curler 24. Consequently, the user is prevented from feeling discomfort due to the wear of the cuff structure 20.

Figure 6:
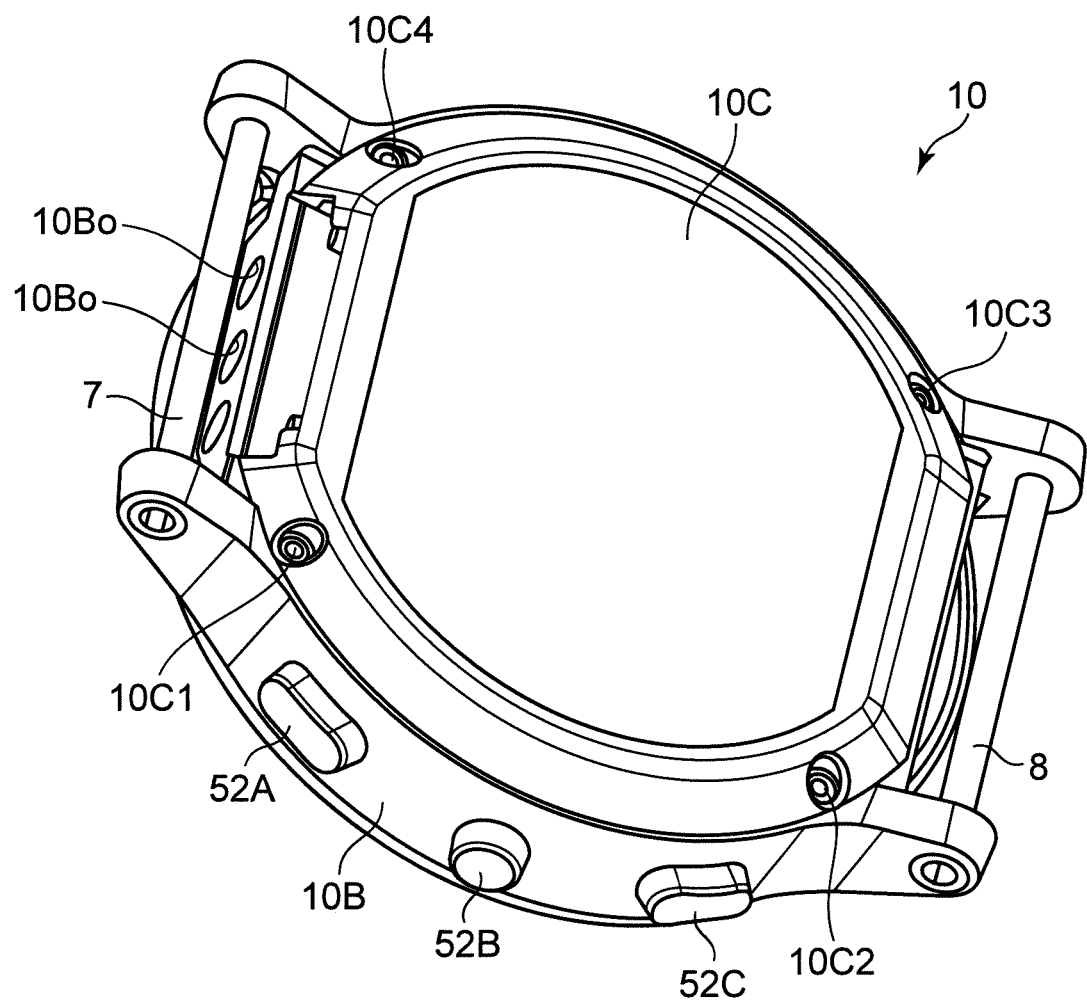
FIG. 6 is a view illustrating a back side of a main body of the sphygmomanometer when the sphygmomanometer is obliquely viewed.
Figure 10:
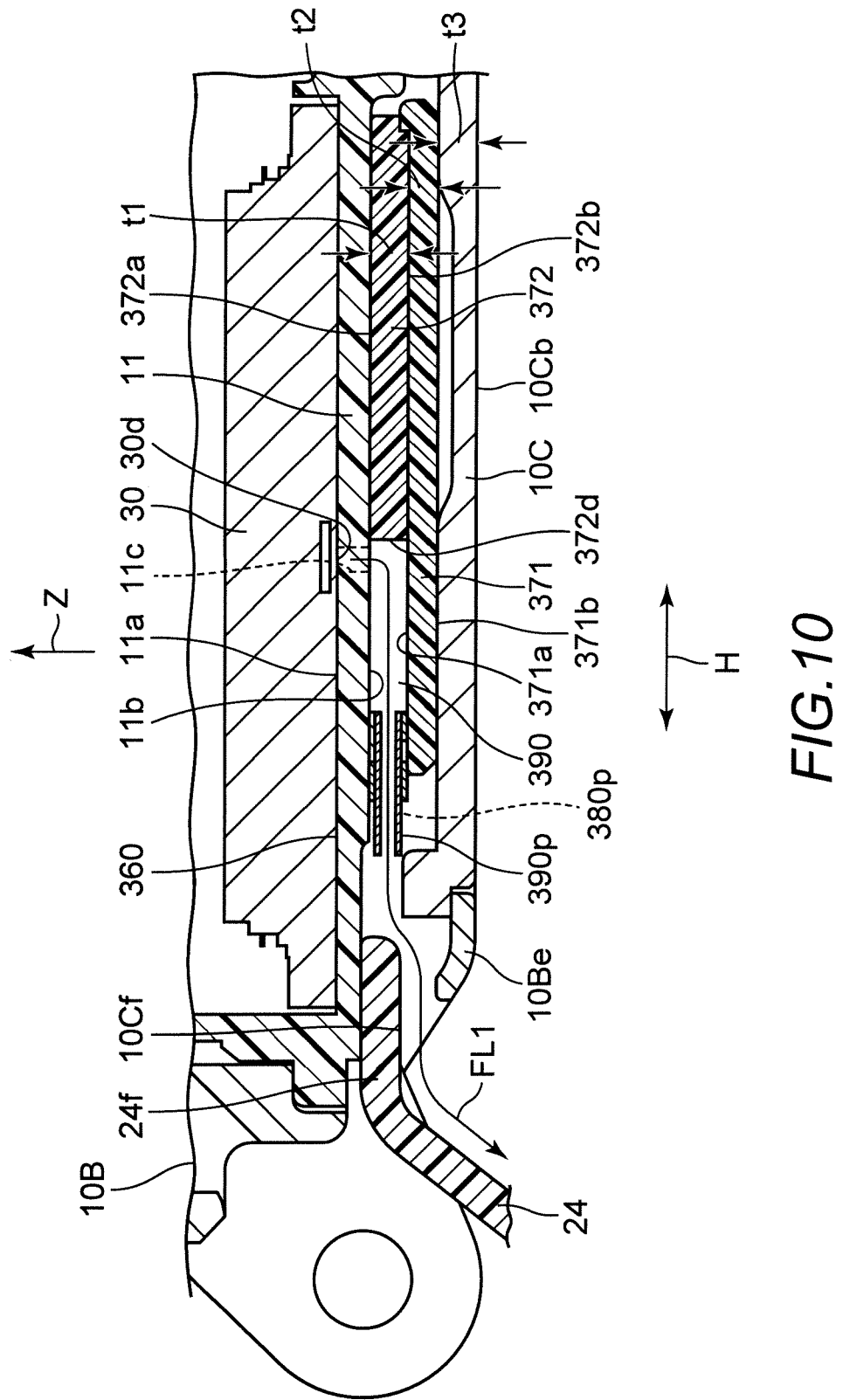
FIG. 10 is a view illustrating a sectional structure in the vicinity of a planar direction passage provided in the main body.
Figure 21:
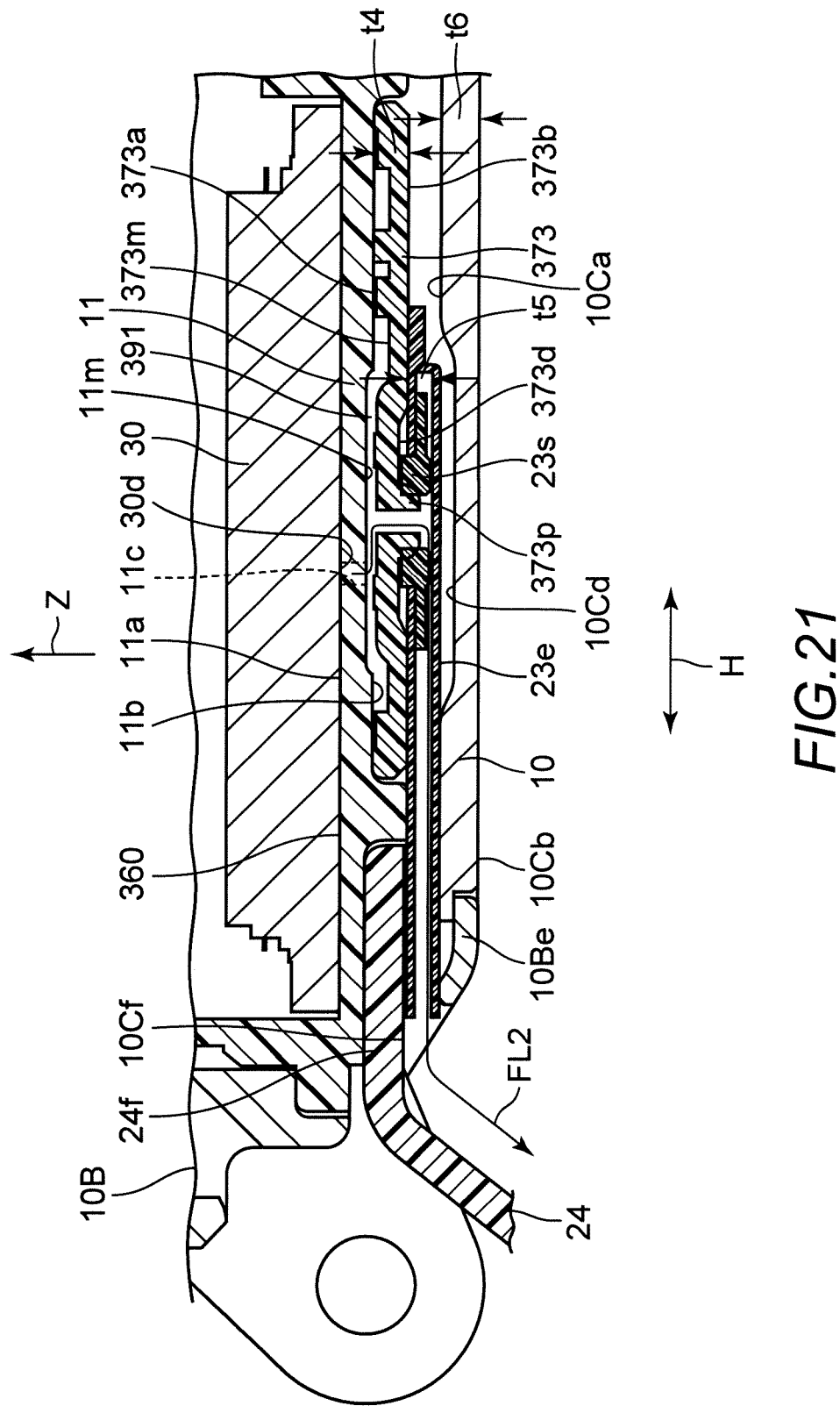
FIG. 21 is a view illustrating a sectional structure in the vicinity of a planar direction passage provided in a main body of a first modification corresponding to FIG. 10.

As illustrated in FIG. 6, the back lid 10C is provided on the back side of the main body 10. The back lid 10C has four through-holes 10C1, 10C2, 10C3, 10C4, and is fixed to the back side of the case 10B by screws (not illustrated) through the through-holes 10C1, 10C2, 10C3, 10C4. Filter-equipped intake and exhaust ports 10Bo, 10Bo, . . . are provided in a portion hidden behind the root 3e of the first belt 3 on the side surface of the case 10B (the same holds true for a portion hidden behind the root 4e of the second belt 4). Consequently, air can flow between the inside and the outside of the case 10B while a domestic water proof function is implemented. As illustrated in FIGS. 10 and 21, an engaging unit 10Be that engages the edge of back lid 10C may be provided in the back side of the case 10B.

FIG. 7 illustrates the back side of the main body 10 including the curler 24 in a disassembled state in which the back lid 10C is removed. An inner case member 11 as a substrate on which the blood pressure measurement element is mounted is accommodated in the case 10B of the main body 10. In this example, the inner case member 11 is made of a synthetic resin (for example, acrylonitrile butadiene styrene (ABS) resin). Three protrusions 11p1, 11p2 and 11p3 are formed on one side (in FIG. 7, a left side) of a back surface 11b of the inner case member 11. A ring 24o having a shape collectively enclosing the three protrusions 11p1, 11p2 and 11p3 is formed in the root 24f of the curler 24. In assembling the main body 10, the three protrusions 11p1, 11p2 and 11p3 of the inner case member 11 is fitted in the ring 24o of the root 24f of the curler 24. The root 24f of the curler 24 is sandwiched between a portion around the three protrusions 11p1, 11p2, 11p3 in the back surface 11b of the inner case member 11 and edges 10Ce, 10Cf on one side of the back lid 10C of the main body 10 opposed to the portion around the three protrusions 11p1, 11p2, 11p3.

Consequently, as illustrated in FIG. 2, one end 20f of the cuff structure 20 (the root 24f of the curler 24) is attached to the main body 10. The other end 20e of the cuff structure 20 (the leading end 24e of the curler 24) is a free end. As a result, the cuff structure 20 is opposed to the inner circumferential surfaces 3a, 4a of the belt 2, and can be separated from the inner circumferential surfaces 3a, 4a.

In the case that the cuff structure 20 is attached to the main body 10 in this way, the one end 20f of the cuff structure 20 is reliably held by the main body 10. At time of maintenance service, by opening the back lid 10C of the main body 10, the cuff structure 20 can be exchanged with respect to the main body 10 regardless of the belt 2. The dimension in the longitudinal direction Y (corresponding to the circumferential direction of the left wrist 90) of the cuff structure 20 can be set to the optimum dimension regardless of the belt 2.

In the sphygmomanometer 1, the main body 10 and the belt 2 are formed separately from each other, and the belt 2 is attached to the main body 10, so that the belt 2 can also be replaced with respect to the main body 10 regardless of the cuff structure 20 during maintenance service.

In FIG. 7, a spacer plate 372 and a plate-shaped member 371 along the back surface 11b of the inner case member 11 are sandwiched between the back surface 11b of the inner case member 11 and the back lid 10C of the main body 10. In this example, the spacer plate 372 is made of a synthetic resin (for example, polyurethane), and the plate-shaped member 371 is also made of a synthetic resin (for example, an ABS resin). Two surfaces 372a, 372b of the spacer plate 372 are in close contact with the back surface 11b of the inner case member 11 and an opposing surface 371a of the plate-shaped member 371 opposed to the back surface 11b, and maintain the inner case member 11 and the plate-shaped member 371 in a state in which the inner case member 11 and the plate-shaped member 371 are separated from each other in a thickness direction Z. At the same time, the spacer plate 372 constitutes two planar direction passages 390, 380 extending in a planar direction H (a direction perpendicular to the thickness direction Z) along between the back surface 11b of the inner case member 11 and the opposing surface 371a of the plate-shaped member 371. That is, the spacer plate 372 includes inner circumferential walls 372d, 372e making two holes penetrating through the spacer plate 372 in the thickness direction Z. The inner circumferential walls 372d, 372e form patterns of a first planar direction passage 390 and a second planar direction passage 380. Cylindrical lateral pins 390p, 380p as the first flow port are integrated with the end of the first planar direction passage 390 and the end of the second planar direction passage 380 so as to allow the fluid to flow. The lateral pins 390p, 380p pierce in the planar direction H between the inner circumferential walls 372d, 372e of the spacer plate 372 and an outer circumferential wall 372f opposed to the inner circumferential walls 372d, 372e (the state in which lateral pins 390p, 380p pierce is illustrated by a broken line in FIG. 9). When the cuff structure 20 including the curler 24 is attached to the main body 10, the flexible tube 39 from the pressing cuff 23 is airtightly fitted to the lateral pin 390p, and is easy to attach. The flexible tube 38 from the sensing cuff 21 is air-tightly fitted to the lateral pin 380p, and is easily attached. Consequently, the pressing cuff 23 and the sensing cuff 21 are communicated with the first planar direction passage 390 and the second planar direction passage 380 through the flexible tubes 39, 38, respectively. The lateral pins 390p, 380p as the first flow port is oriented toward the planar direction H, so that the lateral pins 390p, 380p can contribute to the low profile of the product. In this example, the flexible tubes 39, 38 constitute a first flexible passage. The structure of the passage in the main body 10 will be described later.

(Block Configuration of Control System)

Figure 11:
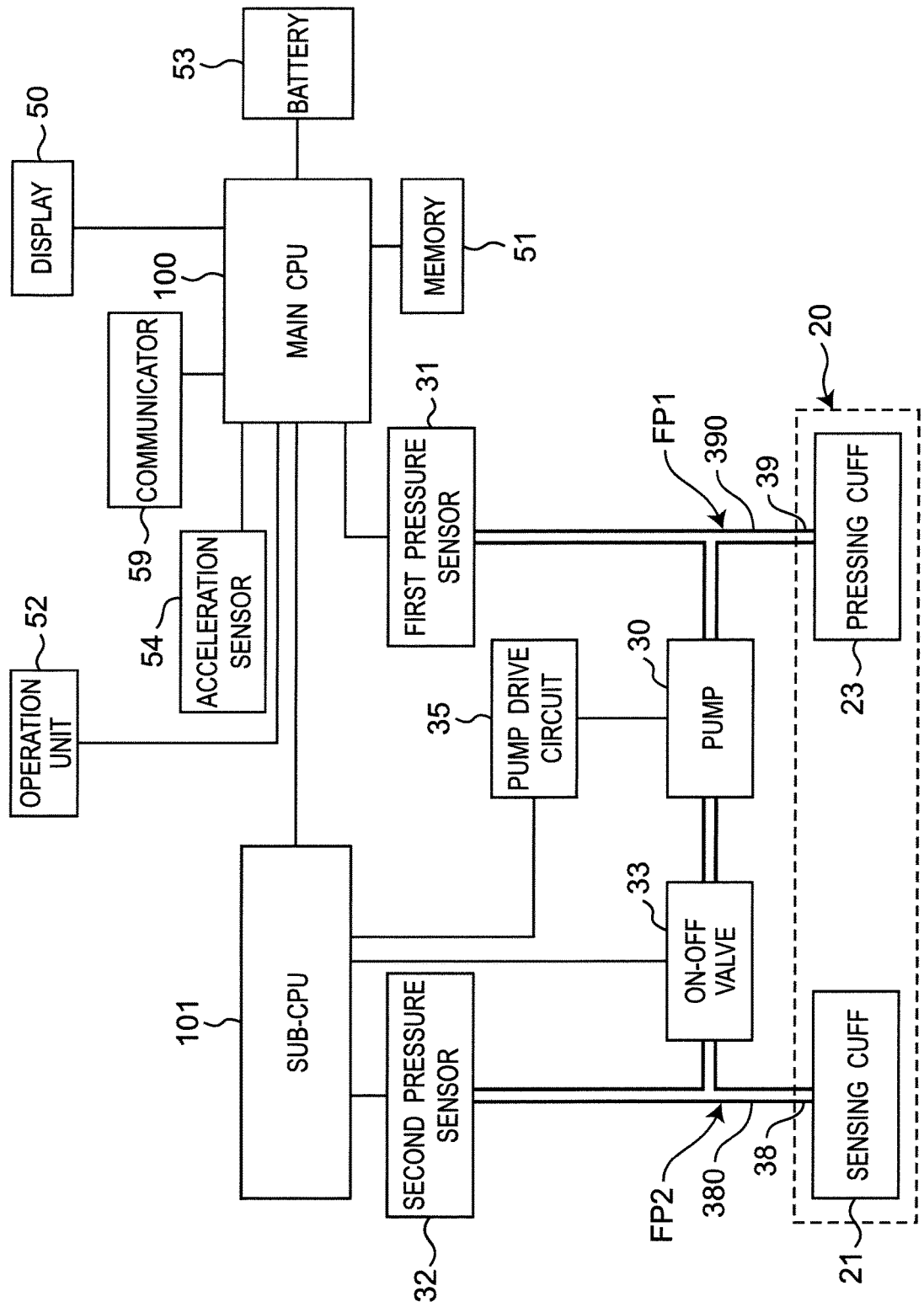
FIG. 11 is a view illustrating a block configuration of a control system of the sphygmomanometer.

FIG. 11 illustrates a block configuration of a control system of the sphygmomanometer 1. In addition to the display 50 and the operation unit 52, a main Central Processing Unit (CPU) 100 as a control unit, a sub-CPU 101, a memory 51 as a storage, an acceleration sensor 54, a communicator 59, a battery 53, a first pressure sensor 31 that detects pressure of the pressing cuff 23, a second pressure sensor 32 that detects pressure of the sensing cuff 21, a pump 30, an On-off valve 33, and a pump drive circuit 35 that drives the pump 30 are mounted as the blood pressure measurement element that performs the blood pressure measurement in the main body 10 of the sphygmomanometer 1. The main CPU 100 mainly controls the operation of the entire sphygmomanometer 1, and the sub-CPU 101 mainly controls the operation of an air system. Hereinafter, for convenience, the main CPU 100 and the sub-CPU 101 will be simply referred to as the CPU 100 in combination.

The display 50 is constructed with a Liquid Crystal Display (LCD) in this example, and displays information related to the blood pressure measurement such as a blood pressure measurement result and other information according to a control signal from the CPU 100. The display 50 is not limited to the LCD, but may be another type of display 50 such as an organic Electro Luminescence (EL) display. The display 50 may include a Light Emitting Diode (LED).

As described above, the operation unit 52 includes the measurement switch 52A that gives an instruction to start or stop the blood pressure measurement, the home switch 52B that returns the display screen of the display 50 to the predetermined home screen, and the recording call switch 52C that instructs the display 50 to display the measurement record such as the blood pressure and the activity mass in the past. In this example, these switches 52A to 52C are constructed with push switches, and input an operation signal to the CPU 100 in response to the instruction such as the start or stop of the blood pressure measurement from the user. The operation unit 52 is not limited to the push switch, but may be constructed with, for example, a pressure-sensitive (resistive) or proximity (electrostatic capacitive) touch panel switch. A microphone (not illustrated) may be provided to input the instruction to start the blood pressure measurement by user's voice.

The memory 51 non-transiently stores data of a program controlling the sphygmomanometer 1, data used to control the sphygmomanometer 1, setting data setting various functions of the sphygmomanometer 1, data of the measurement result of the blood pressure value, and the like. The memory 51 is also used as a work memory or the like when a program is executed.

The CPU 100 performs various functions as a controller according to the program controlling the sphygmomanometer 1 stored in the memory 51. For example, when performing the blood pressure measurement function, the CPU 100 controls drive of the pump 30 and the On-off valve 33 based on the signals from the first pressure sensor 31 and the second pressure sensor 32 in response to the instruction to start the blood pressure measurement from the measurement switch 52A of the operation unit 52. The CPU 100 controls the calculation of the blood pressure value, a pulse, and the like based on a signal from the second pressure sensor 32.

The acceleration sensor 54 is constructed with a three-axis acceleration sensor integrally incorporated in the main body 10. The acceleration sensor 54 outputs an acceleration signal representing the acceleration of the main body 10 in three directions orthogonal to one another to the CPU 100. In this example, the output of the acceleration sensor 54 is used to measure the activity mass.

The communicator 59 is controlled by the CPU 100 to transmit predetermined information to an external device through the network, or to receive information from the external device through the network to deliver the information to the CPU 100. The communication through the network may be conducted in a wireless or wired manner. In this embodiment, the network is the Internet. However, the network is not limited to the Internet, but may be another type of network such as an in-hospital Local Area Network (LAN) or one-to-one communication using a USB cable or the like. The communicator 59 may include a micro USB connector.

In this example, the battery 53 is constructed with a rechargeable secondary battery. The battery 53 supplied power to an element mounted on the main body 10, in this example, each of the elements including the CPU 100, the memory 51, the acceleration sensor 54, the communicator 59, the first pressure sensor 31, the second pressure sensor 32, the pump 30, the On-off valve 33, and the pump drive circuit 35.

The pump 30 is constructed with a piezoelectric pump in this example, and is driven by the pump drive circuit 35 based on a control signal supplied from the CPU 100. The pump 30 is connected to the pressing cuff 23 through the first planar direction passage 390 and the flexible tube 39, which constitute a first passage FP1, so as to be able to pass the fluid to the pressing cuff 23. The pump 30 can supply air as the pressurization fluid to the pressing cuff 23 through the first planar direction passage 390 and the flexible tube 39. An exhaust valve (not illustrated) in which opening and closing are controlled according to on and off of the pump 30 is mounted on the pump 30. That is, the exhaust valve closes to assist sealing of the air in the pressing cuff 23 when the pump 30 is turned on, and the exhaust valve opens to discharge the air in the pressing cuff 23 to atmosphere through the flexible tube 39 and the first planar direction passage 390 when the pump 30 is turned off. The exhaust valve has a function of a check valve, and the air to be discharged does not flow backward.

The pump 30 is connected to the sensing cuff 21 through the second planar direction passage 380 and the flexible tube 38, which constitute a second passage FP2, so as to be able to pass the fluid to the sensing cuff 21. An On-off valve (in this example, a normally open electromagnetic valve) 33 is interposed in the second passage FP2 (in fact, between the first planar direction passage 390 and the second planar direction passage 380). The opening and closing (opening degree) of the On-off valve 33 is controlled based on a control signal supplied from the CPU 100. When the On-off valve 33 is in the open state, the air can be supplied and stored as the pressure transmitting fluid from the pump 30 to the sensing cuff 21 through the second passage FP2.

In this example each of the first pressure sensor 31 and the second pressure sensor 32 is constructed with a piezoresistive pressure sensor. The first pressure sensor 31 detects the pressure in the pressing cuff 23 through the first planar direction passage 390 and the flexible tube 39 that constitute the first passage FP1. The second pressure sensor 32 detects the pressure in the sensing cuff 21 through the second planar direction passage 380 and the flexible tube 38 that constitute the second passage FP2.

The compact sphygmomanometer 1 is integrally configured by mounting the above blood pressure measurement element on the main body 10. Thus, the sphygmomanometer 1 is convenient for the user.

(Structure of Passage in Main Body)

Figure 8:
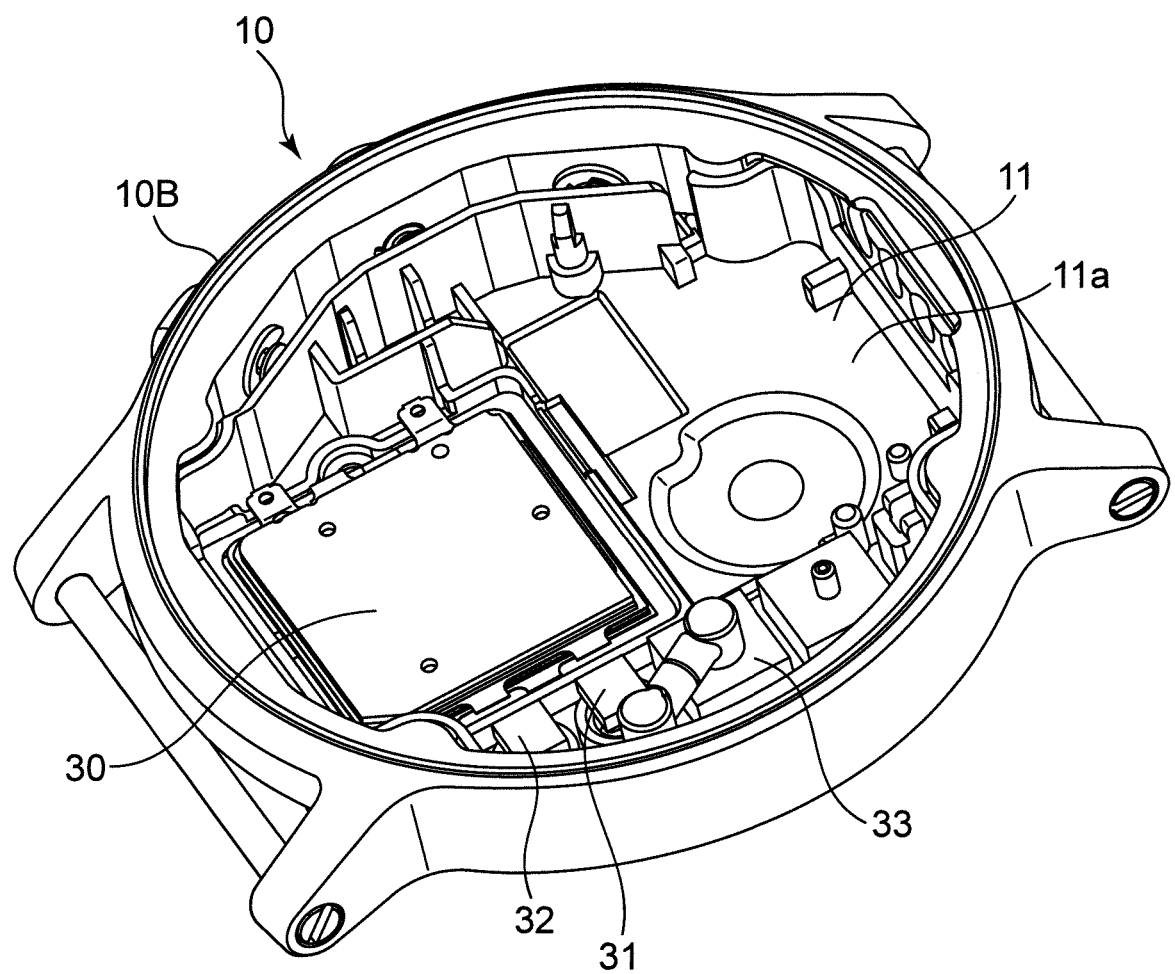
FIG. 8 is a view illustrating an inside of the main body when the main body is viewed obliquely from above.

As illustrated in FIG. 8 (when the inside of the main body 10 is viewed obliquely from above), the pump 30 is disposed in the main body 10 so as to straddle from the substantial center of the surface (one surface) 11a of the inner case member 11 to a left-side periphery (in FIG. 8). The On-off valve 33, the first pressure sensor 31, and the second pressure sensor 32 are disposed along a front-side periphery (in FIG. 8) of the surface 11a of the inner case member 11.

Each of these blood pressure measurement elements 30, 31, 32, 33 has a flat outer shape along the surface 11a of the inner case member 11 in order to achieve the low profile the product. As can be seen from FIG. 9 (the inside of the main body 10 is viewed obliquely from below, for convenience, the plate-shaped member 371 is not illustrated), an air discharge port 30d of the pump 30, an air intake port 31d of the first pressure sensor 31, an air intake port 32d of the second pressure sensor 32, an inlet 33i and an outlet 33e of the On-off valve 33 are provided in an abutting surface that abuts on the surface 11a of the inner case member 11. The inner case member 11 includes a first through-hole 11c at a position corresponding to the air discharge port 30d of the pump 30. The inner case member 11 also includes second through-holes 11d, 11e at positions corresponding to the air intake port 31d of the first pressure sensor 31 and the air intake port 32d of the second pressure sensor 32, respectively. The inner case member 11 includes third through-holes 11g, 11h at positions corresponding to the inlet 33i and the outlet 33e of the On-off valve 33, respectively.

The inner circumferential wall 372d of the spacer plate 372 collectively surrounds the first through-hole 11c, the second through-hole 11d, and the third through-hole 11g in the planar direction H. That is, the first planar direction passage 390 is disposed so as to straddle the air discharge port 30d of the pump 30, the air intake port 31d of the first pressure sensor 31, and the inlet 33i of the On-off valve 33 along the back surface (other surface) 11b of the inner case member 11. The inner circumferential wall 372e of the spacer plate 372 collectively surrounds the second through-hole 11e and the third through-hole 11h in the planar direction H. That is, the second planar direction passage 380 is disposed so as to straddle the outlet 33e of the On-off valve 33 and the air intake port 32d of the second pressure sensor 32 along the back surface 11b of the inner case member 11.

Figure 9:
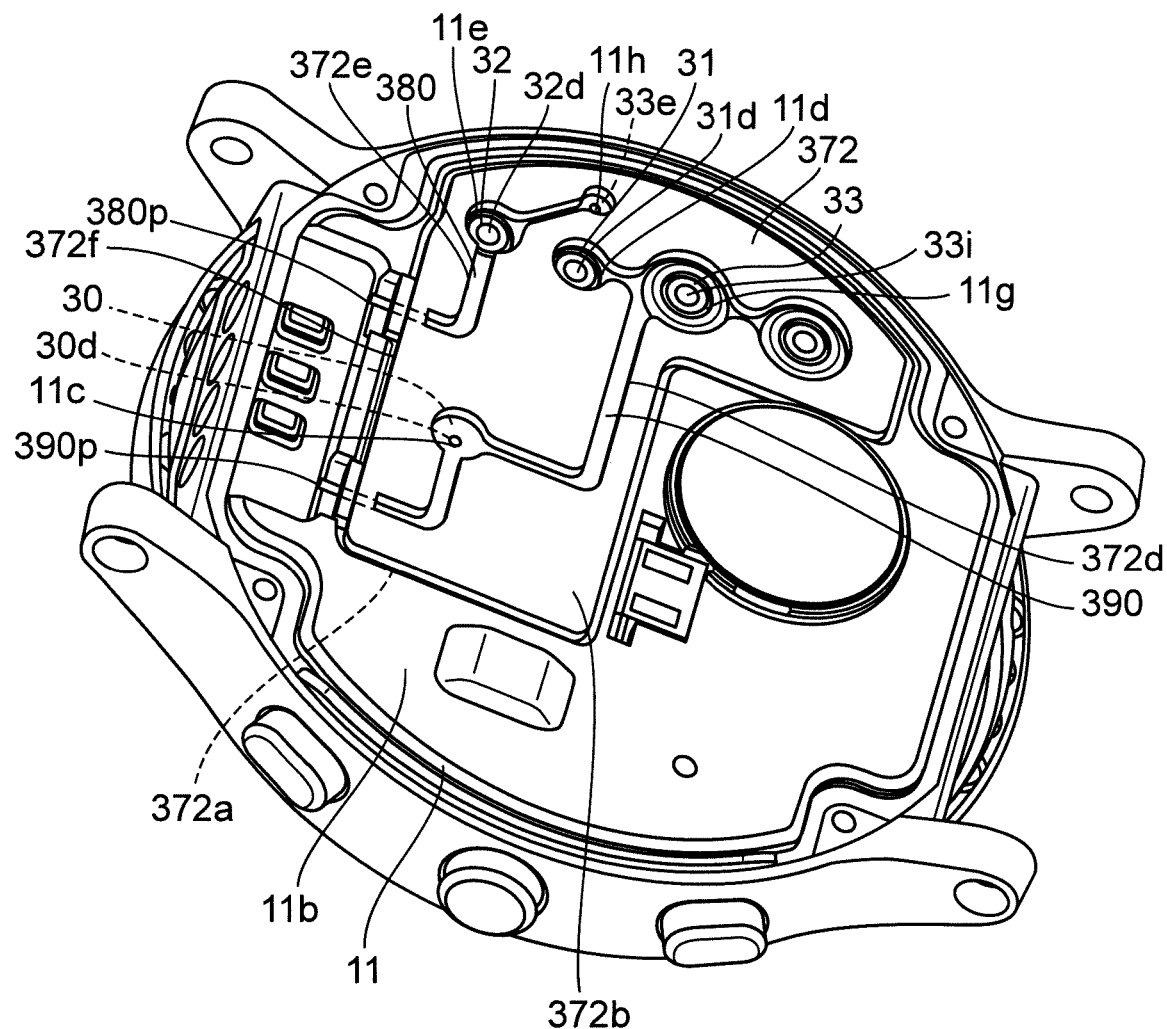
FIG. 9 is a view illustrating the inside of the main body when the main body is viewed obliquely from below.

FIG. 10 illustrates a sectional structure in the vicinity of the first planar direction passage 390 provided in the main body 10. The first planar direction passage 390 is restricted by the back surface 11b of the inner case member 11 and the opposing surface 371a of the plate-shaped member 371 in the thickness direction Z, and restricted by the inner circumferential wall 372d of the spacer plate 372 in the planar direction H. Similarly, the second planar direction passage 380 in FIG. 9 is also restricted by the back surface 11b of the inner case member 11 and the opposing surface 371a of the plate-shaped member 371 in the thickness direction Z, and restricted by the inner circumferential wall 372e of the spacer plate 372 in the planar direction H. In the state in which the main body 10 is assembled, the flexible tubes 39, 38 constituting the first flexible passage are fitted and attached to the lateral pins 390p, 380p as the first flow port, respectively. Consequently, as described above, the first planar direction passage 390 communicates with the pressing cuff 23 through the lateral pin 390p and the flexible tube 39. Similarly, the second planar direction passage 380 communicates with the sensing cuff 21 through the lateral pin 380p and the flexible tube 38.

Thus, during the blood pressure measurement, as illustrated by an arrow FL1 in FIG. 10, the air can be supplied from the air discharge port 30d of pump 30 to the pressing cuff 23 through first through-hole 11c, the first planar direction passage 390, and flexible tube 39. The air can be supplied from the air discharge port 30d of the pump 30 to the sensing cuff 21 through the first through-hole 11c, the first planar direction passage 390, the On-off valve 33 in the open state, the second planar direction passage 380, and the flexible tube 38. At this point, the air is introduced from the pressing cuff 23 to the air intake port 31d of the first pressure sensor 31 through the flexible tube 39, the first planar direction passage 390, and the second through-hole 11d. The air is introduced from the sensing cuff 21 to the air intake port 32d of the second pressure sensor 32 through the flexible tube 38, the second planar direction passage 380, and the second through-hole 11e. Thus, the pressures of the pressing cuff 23 and the sensing cuff 21 are detected by the first pressure sensor 31 and the second pressure sensor 32, respectively.

In this example, the thickness of the spacer plate 372 in FIG. 10 is set to t1=0.8 mm, the thickness of the plate-shaped member 371 is set to t2=0.6 mm, and the thickness of the back lid 10C is set to t3=0.8 mm. Thus, the thickness from the back surface 11b of the inner case member 11 to an outer surface 10Cb of the back lid 10C becomes t1+t2+t3=2.2 mm. Consequently, the low profile of the product can be achieved.

As illustrated in FIG. 10, an adhesive 360 as a sealing unit is provided between the surface 11a of the inner case member 11 and the abutting surface around the air discharge port 30d of the pump 30. Thus, the pump 30 is attached to the surface 11a of the inner case member 11 in a fluid tight manner (in this example, airtight). Although not illustrated, similarly an adhesive as the sealing unit is provided between the surface 11a of the inner case member 11 and the abutting surface around the air intake port 31d of the first pressure sensor 31, the abutting surface around the air intake port 32d of the second pressure sensor 32, and the abutting surface around the inlet 33i and the outlet 33e of the On-off valve 33. Consequently, the first pressure sensor 31, the second pressure sensor 32, and the On-off valve 33 are attached to the surface 11a of the inner case member 11 in the fluid tight manner (in this example, airtight). As a result, the air is prevented from leaking between the surface 11a of the inner case member 11 and the abutting surfaces of the blood pressure measurement elements 30, 31, 32, 33.

In this example, the plate-shaped member 371 is made of a synthetic resin. However, the present invention is not limited to the embodiment. The plate-shaped member 371 may include a layer made of stainless steel or another metal to increase mechanical strength of the plate-shaped member 371. Consequently, the thickness of the plate-shaped member 371 can be set thinner as compared with the case that the plate-shaped member 371 is made of only a general synthetic resin material. As a result, the low profile of the product can further be achieved.

(Operation of Blood Pressure Measurement)

Figure 12:
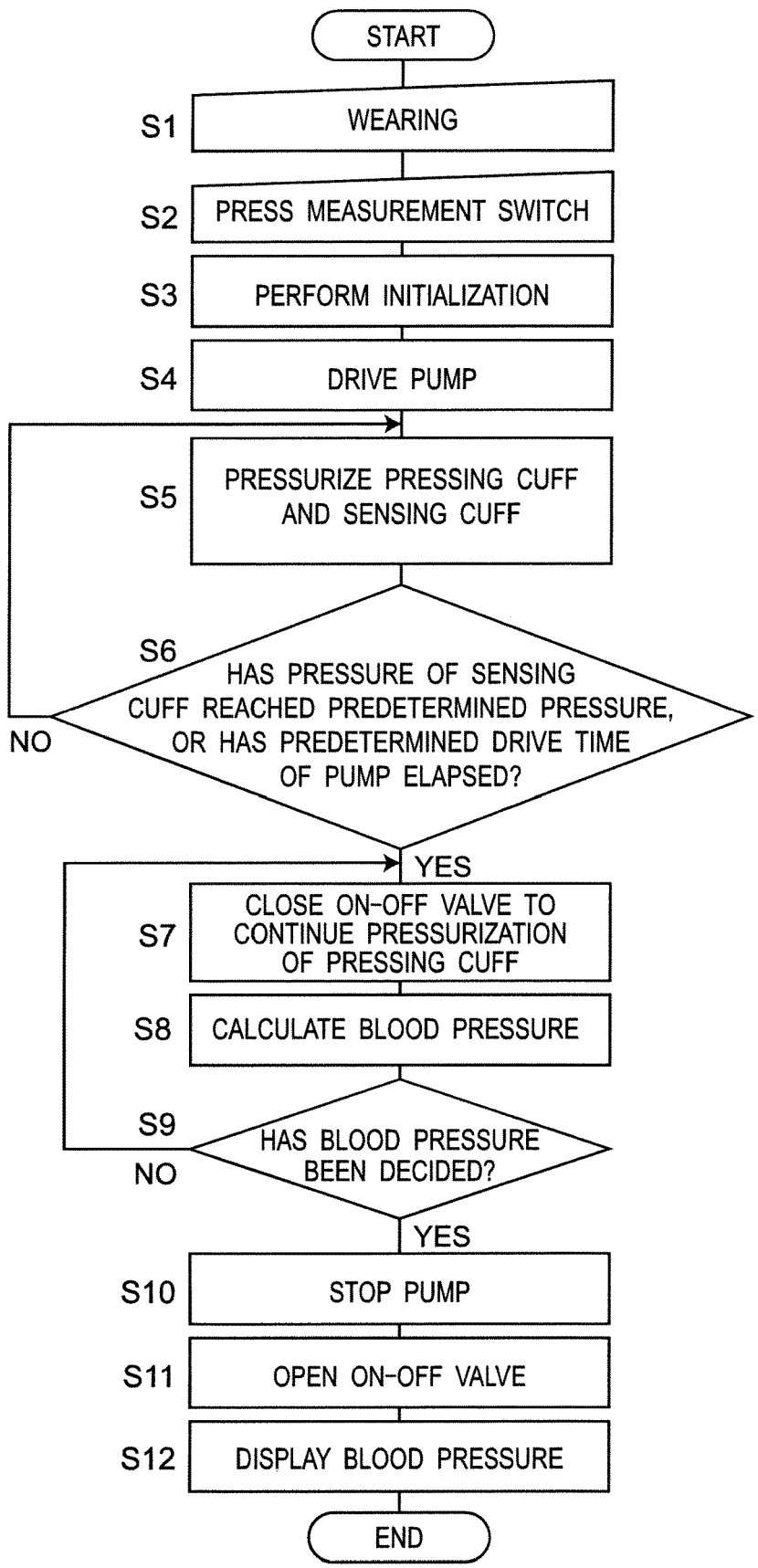
FIG. 12 is a flowchart illustrating an operation when a user performs blood pressure measurement with the sphygmomanometer as a blood pressure measurement method according to an embodiment of the present invention.

FIG. 12 illustrates a flowchart when the user performs blood pressure measurement with the sphygmomanometer 1.

As illustrated in step S1 of FIG. 12, the user wears the sphygmomanometer 1 on the left wrist 90 as the measured site. In wearing the sphygmomanometer 1, as illustrated in FIG. 14A, the user wears the cuff structure 20 on the left wrist 90 using a right hand 99 (step S21 in FIG. 13). At this point, in the natural state, the cuff structure 20 is curved along the circumferential direction Y of the left wrist 90 by the curler 24. Thus, in this example, the user fits the cuff structure 20 in the outer circumferential surface of the left wrist 90 using the hand (in this example, the right hand 99) of a right half body on the opposite side of a left half body on the side to which the left wrist 90 belongs, which allows the cuff structure 20 to be easily worn on the left wrist 90. In the state in which the cuff structure 20 is worn on the left wrist 90, the cuff structure 20 grips the left wrist 90 even if the user releases the right hand 99 from the cuff structure 20, so that the cuff structure 20 (and the belt 2 and the main body 10) hardly comes off from the left wrist 90.

Subsequently, as illustrated in FIG. 14B, the user collectively bonds the left wrist 90 and the cuff structure 20 with the belt 2 using the right hand 99. Specifically, a portion connected to the leading end 4f of the second belt 4 is passed through the frame-shaped body 5A of the tail lock 5 of the first belt 3, and the prong 5B of the tail lock 5 is inserted into one of the plurality of small holes 4w, 4w, . . . of the second belt 4. Consequently, as illustrated to FIG. 14C, the first belt 3 and the second belt 4 are fastened (step S22 in FIG. 13). Consequently, the belt 2 extending from the main body 10 binds the left wrist 90, and the belt-shaped cuff structure 20 in which the one end 20f is attached to the main body 10 is disposed on the inner circumferential side closer to the left wrist 90 than the belt 2.

In the sphygmomanometer 1, the cuff structure 20 can be separated from the inner circumferential surfaces 3a, 4a of the belt 2, and the other end 20e on the opposite side of the one end 20f of the cuff structure 20 becomes a free end. Thus, when the first belt 3 and the second belt 4 are fastened, the cuff structure 20 receives inward force from the belt 2, and the cuff structure 20 can be slid or deformed just along the outer circumferential surface of the left wrist 90. Consequently, in the worn state, the cuff structure 20 and the belt 2 are in substantially close contact with the outer circumferential surface of the left wrist 90 in this order. In this way, the sphygmomanometer 1 can easily be worn on the left wrist 90.

Figure 15:
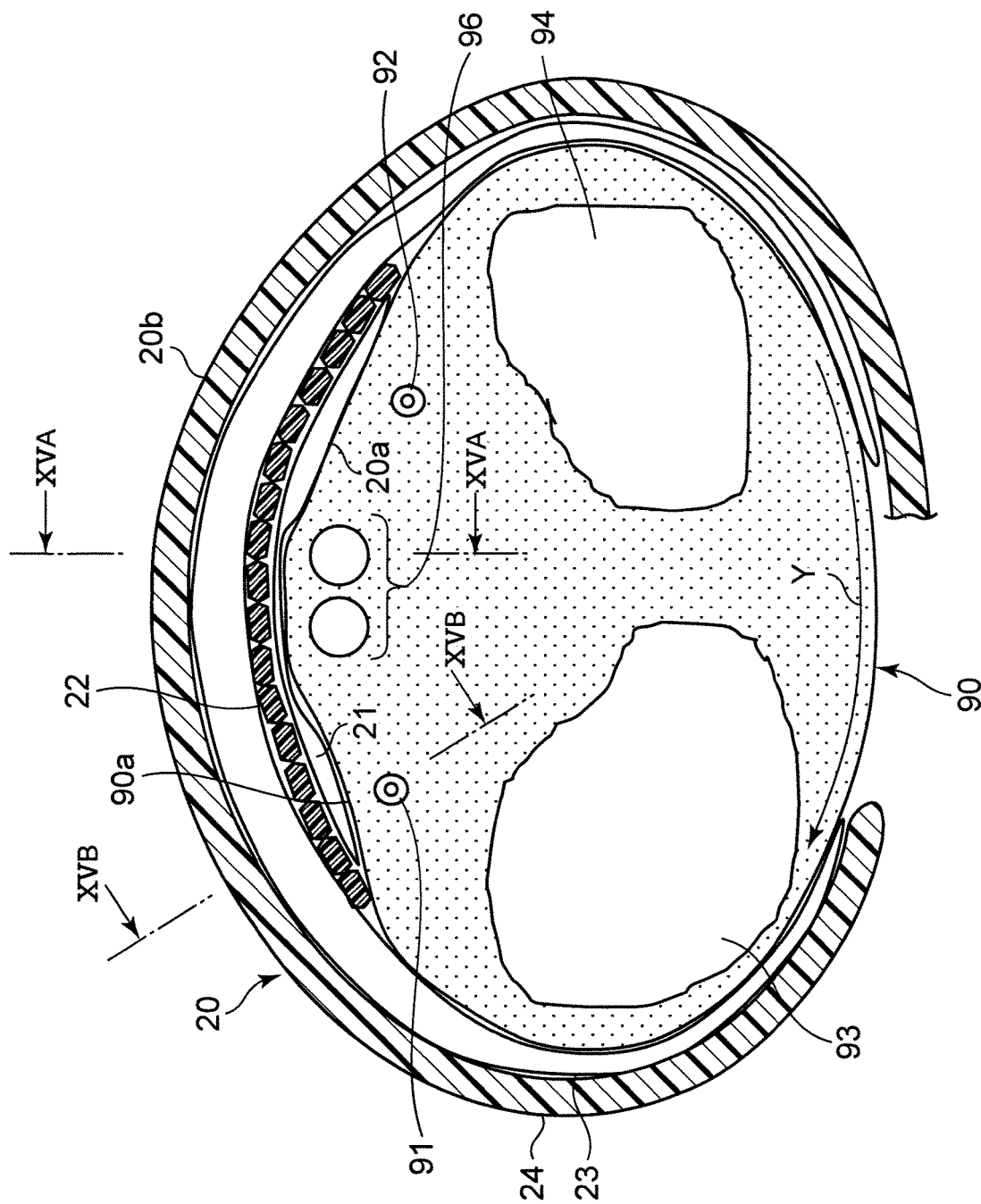
FIG. 15 is a view illustrating a section perpendicular to the left wrist while the sphygmomanometer is worn on the left wrist of the user.

Specifically, as illustrated in FIG. 15, in the worn state, the bag-shaped pressing cuff 23 extends along the circumferential direction Y of the left wrist 90 on the inner circumferential side of the curler 24 included in the cuff structure 20. The bag-shaped sensing cuff 21 included in the cuff structure 20 is disposed on the inner circumferential side with respect to the pressing cuff 23 to contact with the left wrist 90, and extends in the circumferential direction Y so as to cross an artery passage portion 90a of the left wrist 90. The backboard 22 included in the cuff structure 20 is interposed between the pressing cuff 23 and the sensing cuff 21, and extends along the circumferential direction Y of the left wrist 90. The main body 10 and the belt 2 are not illustrated in FIG. 15. A radius 93, an ulna 94, a radial artery 91, an ulnar artery 92, and a tendon 96 of the left wrist 90 are illustrated in FIG. 15.

When the user presses the measurement switch 52A of the operation unit 52 provided in the main body 10 (step S2 in FIG. 12), the CPU 100 initializes a processing memory area (step S3 in FIG. 12). The CPU 100 turns off the pump 30 through the pump drive circuit 35 to open the exhaust valve built in the pump 30, and maintains the On-off valve 33 in the open state to discharge the air in the pressing cuff 23 and the sensing cuff 21. Subsequently, adjustment of 0 mmHg of the first pressure sensor 31 and the second pressure sensor 32 is controlled.

Subsequently, the CPU 100 acts as a pressurization controller and a fluid storage controller to turn on the pump 30 through the pump drive circuit 35 (step S4 in FIG. 12), and maintains the On-off valve 33 in the open state to start the pressurization of the pressing cuff 23 and the sensing cuff 21 (step S5 in FIG. 12). In a pressurization process, the pump 30 is driven through the pump drive circuit 35 while the pressures of the pressing cuff 23 and the sensing cuff 21 are monitored by the first pressure sensor 31 and the second pressure sensor 32, respectively. Consequently, the control is performed such that the air is sent to the pressing cuff 23 through the first passage FP1 (including the first planar direction passage 390 and the flexible tube 39), and such that the air is sent to the sensing cuff 21 through the second passage FP2 (including the second planar direction passage 380 and the flexible tube 38). Consequently, the air can successfully be supplied from the pump 30 to the pressing cuff 23 and the sensing cuff 21.

Subsequently, in step S6 of FIG. 12, the CPU 100 acts as the fluid storage controller to determine whether the pressure of the sensing cuff 21 has reached a predetermined pressure (in this example, 15 mmHg) or whether a predetermined drive time of the pump 30 has elapsed (in this example, 3 seconds). The reason the determination is made is that it is required to check whether an appropriate amount of air has been stored in the sensing cuff 21. When the negative determination is made in step S6 of FIG. 12, the processing waits until the pressure of the sensing cuff 21 reaches a predetermined pressure or the predetermined drive time of the pump 30 elapses. The "appropriate amount" of the pressure transmitting fluid stored in the sensing cuff 21 will be described later.

Figure 17:
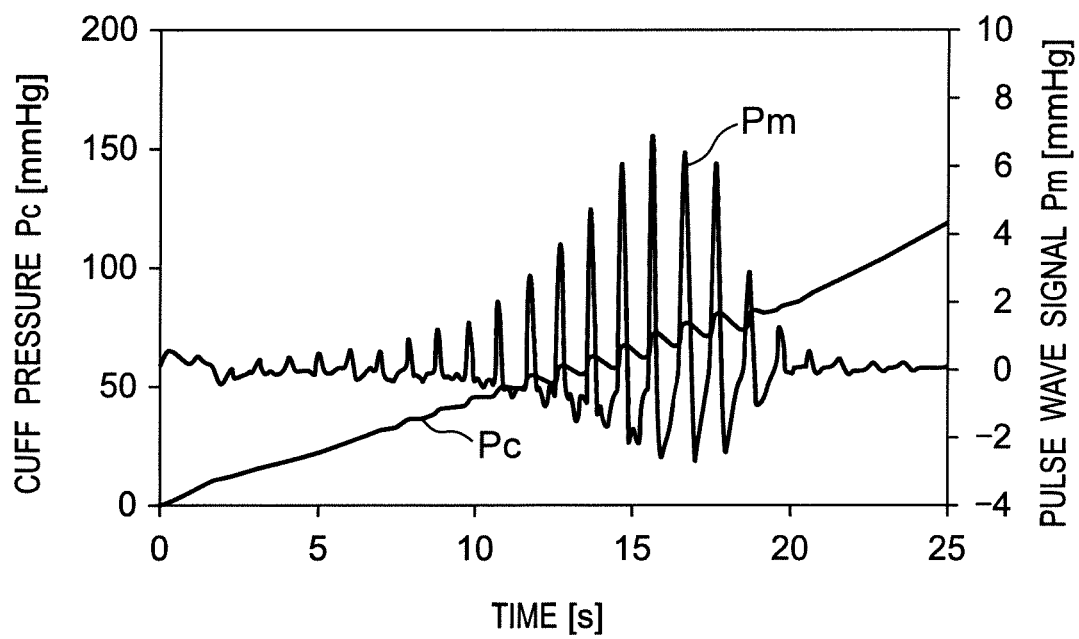
FIG. 17 is a view illustrating a pressure Pc of a sensing cuff and a pulse wave signal Pm that are detected by a second pressure sensor mounted on the main body.

When the affirmative determination is made in step S6 of FIG. 12, it is determined that the appropriate amount of air has been stored in the sensing cuff 21. In step S7 of FIG. 12, the CPU 100 acts as the pressurization controller, closes the On-off valve 33, and continues the control of supplying the air from the pump 30 to the pressing cuff 23 through the first passage FP1. Consequently, the pressing cuff 23 is inflated and the pressure is gradually applied to press the left wrist 90. At this point, the backboard 22 transmits the pressing force from the pressing cuff 23 to the sensing cuff 21. The sensing cuff 21 presses the left wrist 90 (including the artery passage portion 90a). In the pressurization process, the CPU 100 monitors a pressure Pc of the sensing cuff 21, namely, the pressure of the artery passage portion 90a of the left wrist 90 using the second pressure sensor 32 in order to calculate the blood pressure value, and acquire a pulse wave signal Pm as a fluctuation component. FIG. 17 illustrates waveforms of the pressure Pc of the sensing cuff 21 and the pulse wave signal Pm obtained in this pressurization process.

Figure 16A:
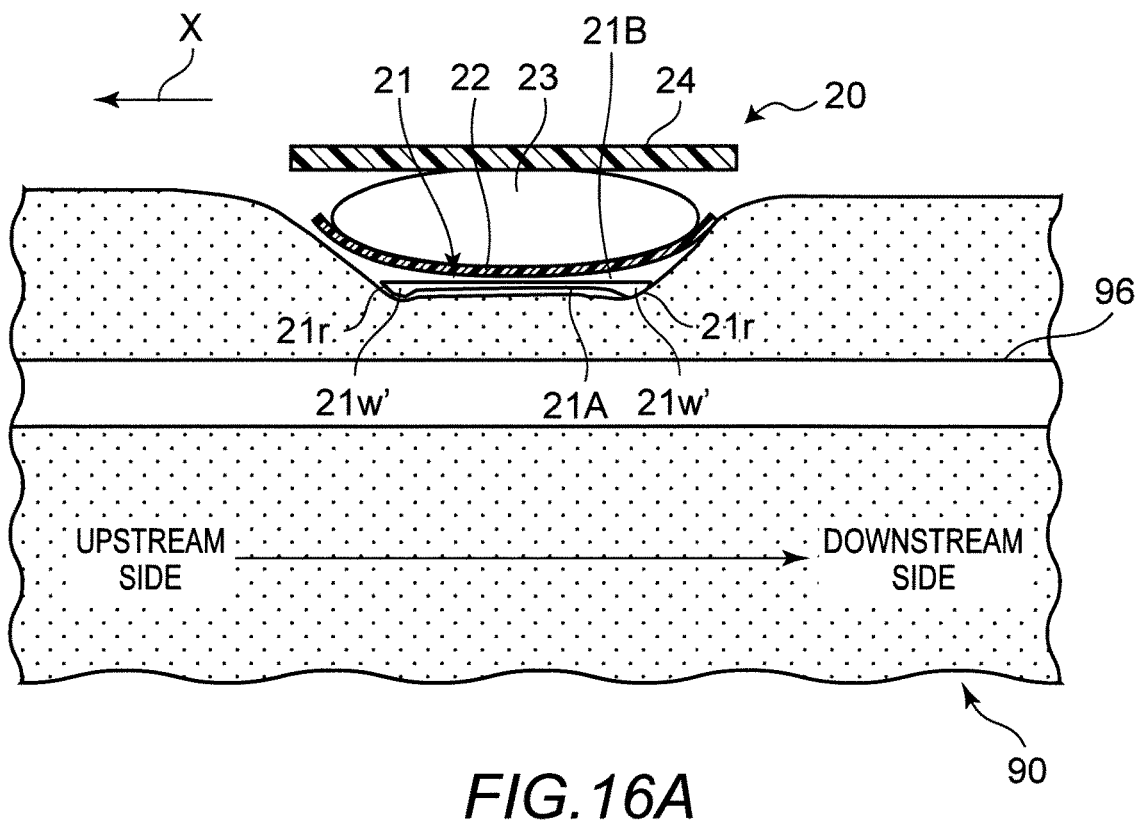
FIG. 16A is a view illustrating a section (corresponding to a section taken along a line XVA-XVA in FIG. 15) of a portion through which a tendon of the left wrist passes in a pressurized state.
Figure 16B:
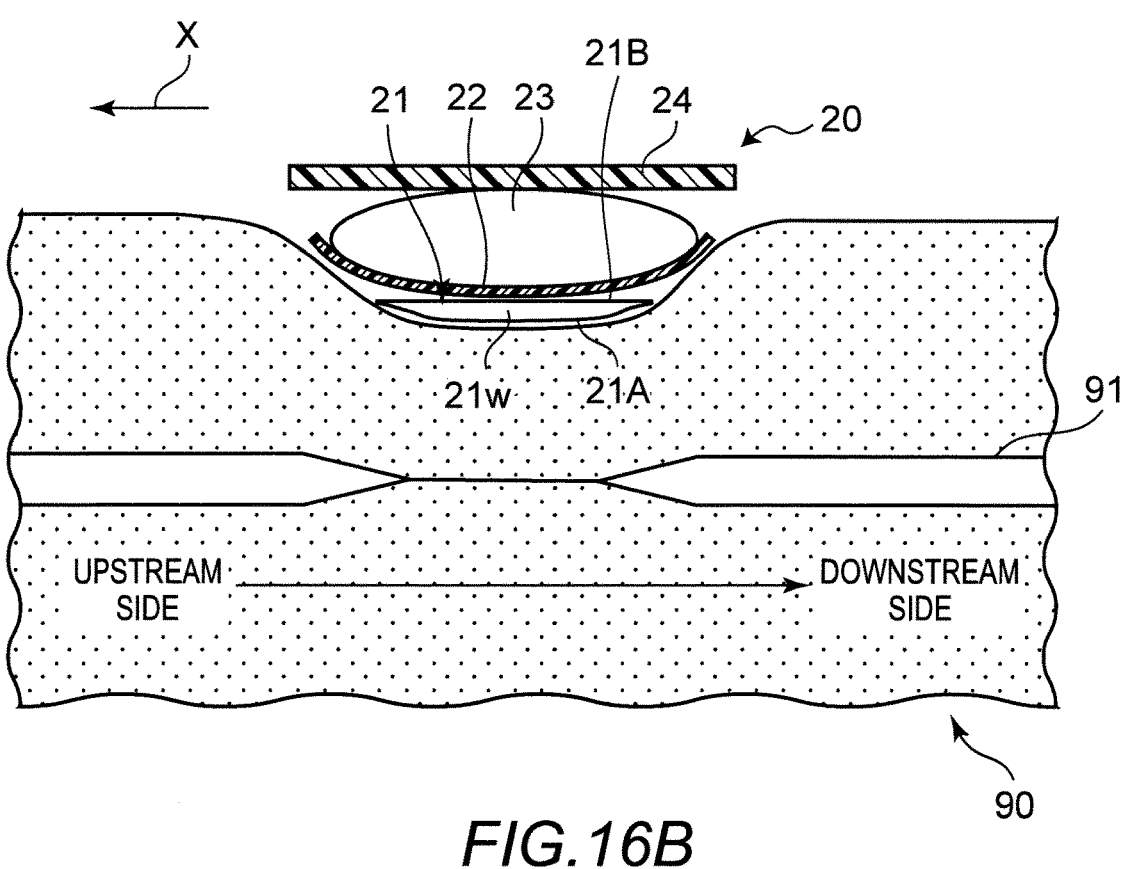
FIG. 16B is a view illustrating a section (corresponding to a section taken along a line XVB-XVB in FIG. 15) of a portion through which a radial artery of the left wrist passes in the pressurized state.

FIGS. 16A and 16B schematically illustrate a section along the longitudinal direction (corresponding to the width direction X of the cuff) of the left wrist 90, in the pressurized state in which an appropriate amount of air is stored in the sensing cuff 21 and the On-off valve 33 is closed. FIG. 16A illustrates a section (corresponding to a section taken along a line XVA-XVA in FIG. 15) of a portion through which the tendon 96 of the left wrist 90 passes. On the other hand, FIG. 16B illustrates a section (corresponding to a section taken along a line XVB-XVB in FIG. 15) of a portion through which the radial artery 91 of the left wrist 90 passes. As illustrated in FIG. 16B, the portion through which the radial artery 91 of the left wrist 90 passes is relatively soft, so that a gap 21w in which air exists remains between the first sheet 21A and the second sheet 21B of the sensing cuff 21. Thus, the portion of the sensing cuff 21 opposed to the radial artery 91 can reflect the pressure of the artery passage portion 90a of the left wrist 90. On the other hand, as illustrated in FIG. 16A, the portion through which the tendon 96 of the left wrist 90 passes is relatively hard, so that the first sheet 21A and the second sheet 21B contact with each other in a portion corresponding to the substantial center in the width direction X of the sensing cuff 21. However, at the place continuous with the edges 21m, 21m on both sides in the width direction X of the sensing cuff 21, gaps 21w', 21w' in which air exists along the longitudinal direction Y remain because the sags 21r, 21r extending along the longitudinal direction Y (corresponding to the circumferential direction of the left wrist 90) are provided as described above. As a result, the air stored in the sensing cuff 21 can flow along the longitudinal direction Y of the sensing cuff 21 through the gaps 21w', 21w'. Thus, the sensing cuff 21 can successfully transmit the pressure applied to the artery passage portion 90a of the left wrist 90 to the second pressure sensor 32 in the main body 10 as the pressure of the air (the pressure transmitting fluid).

Subsequently, in step S8 of FIG. 12, the CPU 100 acts as a blood pressure calculator, and applies a known algorithm by an oscillometric method to try to calculate the blood pressure value (a systolic blood pressure SBP and a diastolic blood pressure DBP) based on the pulse wave signal Pm acquired at this time.

At this point, when the blood pressure value cannot be calculated because of insufficient data (NO in step S9), the pieces of processing in steps S7 to S9 are repeated as long as the cuff pressure does not reach an upper limit pressure (for safety, for example, 300 mmHg is previously decided).

When the blood pressure value can be calculated (YES in step S9), the CPU 100 stops the pump 30 (step S10), opens the On-off valve 33 (step S11), and performs the control of discharging the air in the pressing cuff 23 and the sensing cuff 21. Finally, a measurement result of the blood pressure value is displayed on the display 50 (step S12).

The blood pressure calculation may be performed in not the pressurization process of the pressing cuff 23 but a decompression process.

As described above, in the sphygmomanometer 1, the air is stored in the sensing cuff 21 every time the blood pressure is measured, and the second pressure sensor 32 detects the pressure Pc of the sensing cuff 21, namely, the pressure itself of the artery passage portion 90a of the left wrist 90 separately from the pressing cuff 23. Thus, as a result of setting of a smaller dimension (for example, about 25 mm) in the width direction X of the cuff CF (including the belt 2 and the cuff structure 20), the blood pressure can accurately be measured even if the pressing cuff 23 is largely inflated in the thickness direction to generate a compression loss during the pressurization. In the wear state, the sensing cuff 21 extends in the circumferential direction Y so as to cross the artery passage portion 90a of the left wrist 90. Thus, when the user actually wears the sphygmomanometer 1 on the left wrist 90, even if the cuff is displaced to some extent in the circumferential direction Y of the left wrist 90 along with the main body 10, the sensing cuff 21 does not come off from the artery passage portion 90a of the left wrist 90. Thus, the blood pressure measurement value can be prevented from varying with respect to the actual blood pressure, and resultantly the blood pressure can accurately be measured.

In the above example, each time the blood pressure is measured, the air as the pressure transmitting fluid is stored in the sensing cuff 21, and the air is discharged after the measurement is completed. However, the present invention is not limited to the above example. The pressure transmitting fluid may be stored in the sensing cuff 21 and sealed at a manufacturing stage of the sphygmomanometer 1.

(Appropriate Amount of Pressure Transmitting Fluid Stored in Sensing Cuff)

Figure 18:
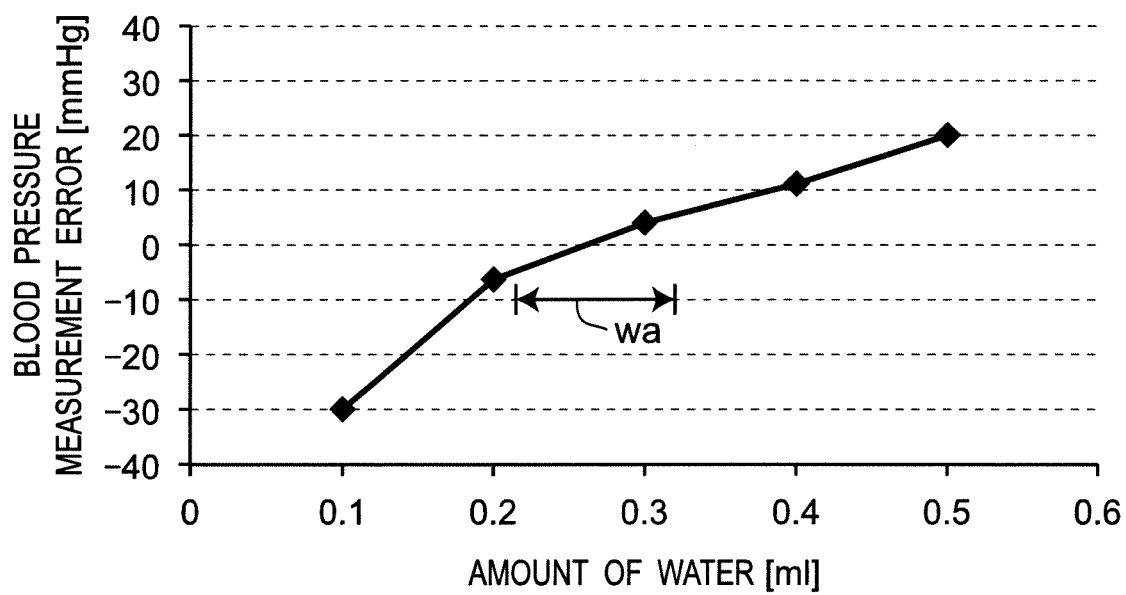
FIG. 18 is a view illustrating a blood pressure measurement error when water is used as a pressure transmitting fluid stored in the sensing cuff and an amount of water stored in the sensing cuff is variably set.

FIG. 18 illustrates a blood pressure measurement error (average value) when water is used as a pressure transmitting fluid stored in the sensing cuff 21 and an amount of water stored in the sensing cuff 21 is variably set. As used herein, the blood pressure measurement error means a difference obtained by subtracting a blood pressure value (a systolic blood pressure SBP, this is referred to as a "reference blood pressure value") measured by a standard (correct) sphygmomanometer from a blood pressure value (systolic blood pressure SBP) measured by the sphygmomanometer 1 for a certain user (subject). That is, (blood pressure measurement error)=(blood pressure value measured by sphygmomanometer 1)−(reference blood pressure value).

As can be seen from FIG. 18, when the amount of water stored in the sensing cuff 21 falls within a range wa of 0.26 ml±0.05 ml, the blood pressure measurement error is within ±5 mmHg, which is considered to be an appropriate amount.

In FIG. 18, when the amount of water exceeds the appropriate range wa, the blood pressure measurement error increases on the positive side. This is attributed to the fact that the water also exists on a hard portion such as the tendon 96 in the section of FIG. 15 to increase the internal pressure of the sensing cuff 21 during the pressurization, and that because the portion through which the radial artery 91 and the ulnar artery 92 in the left wrist 90 pass is relatively soft, the water more than necessary exists in the portion to inflate the sensing cuff 21, and the internal pressure of the sensing cuff 21 is increased by the amount of inflating tension. In FIG. 18, when the amount of water falls below the appropriate range wa, the blood pressure measurement error increases on the negative side. This is attributed to the fact that the amount of water around the artery becomes too small.

As a result, in this example, it is considered that the pressure transmitting fluid stored in the sensing cuff 21 has the suitable range wa of 0.26 ml±0.05 ml. A criterion for a determination whether the pressure of the sensing cuff 21 has reached a predetermined pressure (in this example, 15 mmHg) or a determination whether a predetermined drive time of the pump 30 has elapsed (in this example, 3 seconds) in step S6 of FIG. 12 described above is set so as to satisfy the condition that the amount of air as the pressure transmitting fluid stored in the sensing cuff 21 falls within the range wa of 0.26 ml±0.05 ml.

The appropriate amount of pressure transmitting fluid stored in the sensing cuff 21 depends on a size of the sensing cuff 21 and the like.

(Verification Result)

Figure 19:
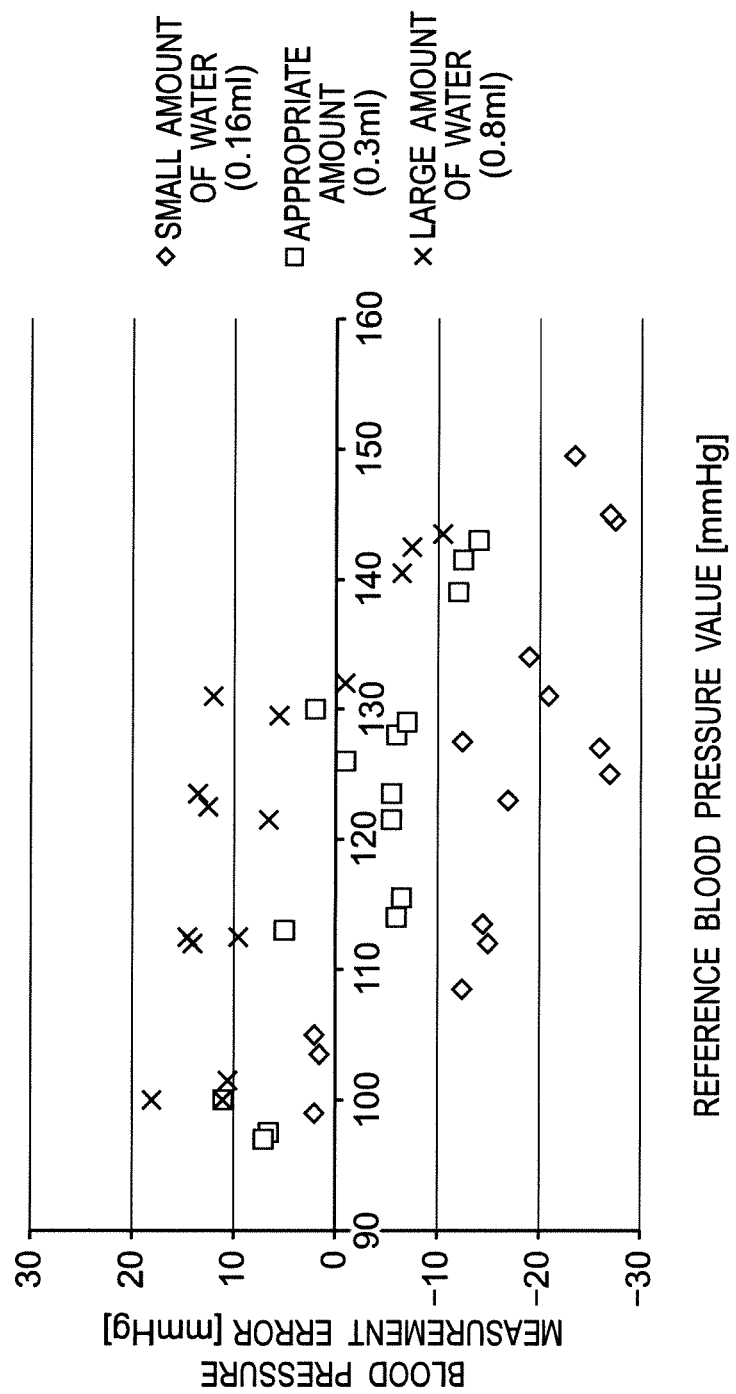
FIG. 19 is a scatter diagram illustrating a relationship between a reference blood pressure value and a blood pressure measurement error when the amount of water stored in the sensing cuff is variably set to "small amount of water"=0.16 ml, "appropriate amount"=0.3 ml, "large amount of water"=0.8 ml for a plurality of users.

The scatter diagram in FIG. 19 illustrates a relationship between the reference blood pressure value and the blood pressure measurement error when the amount of water as the pressure transmitting fluid stored in the sensing cuff 21 is variably set to "small amount of water"=0.16 ml, "appropriate amount"=0.3 ml, "large amount of water"=0.8 ml with respect to a plurality of users (in this example, measurement is performed three times for each of five subjects whose systolic blood pressure SBP ranges from 97 mmHg to 149 mmHg). When the amount of water is "appropriate", as illustrated by a □ sign in FIG. 19, the blood pressure measurement errors are decreased for the plurality of users. On the other hand, in the case of the "large amount of water", as illustrated by a X sign in FIG. 19, the blood pressure measurement errors for the plurality of users are increased on the positive side. In the case of the "small amount of water", as illustrated by a ◇ sign in FIG. 19, the blood pressure measurement errors for the plurality of users are increased on the negative side.

From this verification result, in the sphygmomanometer 1 of the embodiment of the present invention, it can be said that the blood pressure can accurately be measured even if the dimension in the width direction X of the cuff is set small (in this example, the substantial dimension in the width direction of the sensing cuff 21 is set to W4=15 mm and the substantial dimension in the width direction of the pressing cuff 23 is set to W2=25 mm).

In particular, when the plurality of users actually wear the sphygmomanometer 1 on the left wrist 90 to measure the blood pressure, some users may displace the cuff together with the main body 10 to a certain extent in the circumferential direction Y of the left wrist 90. At this point, in the verification result of FIG. 19, when the amount of water is appropriate, the blood pressure measurement errors are suppressed for the plurality of users. Thus, in the sphygmomanometer 1, it is possible to confirm that the blood pressure can accurately be measured even if the cuff is displaced along with the main body 10 to some extent in the circumferential direction Y of the left wrist 90.

First Modification

A first modification in which the structure of the planar direction passage in the main body 10 is modified will be described below. It is assumed that the disposition of the blood pressure measurement elements 30, 31, 32, 33 mounted on the surface 11a of the inner case member 11 in FIG. 8 is maintained.

Figure 20:
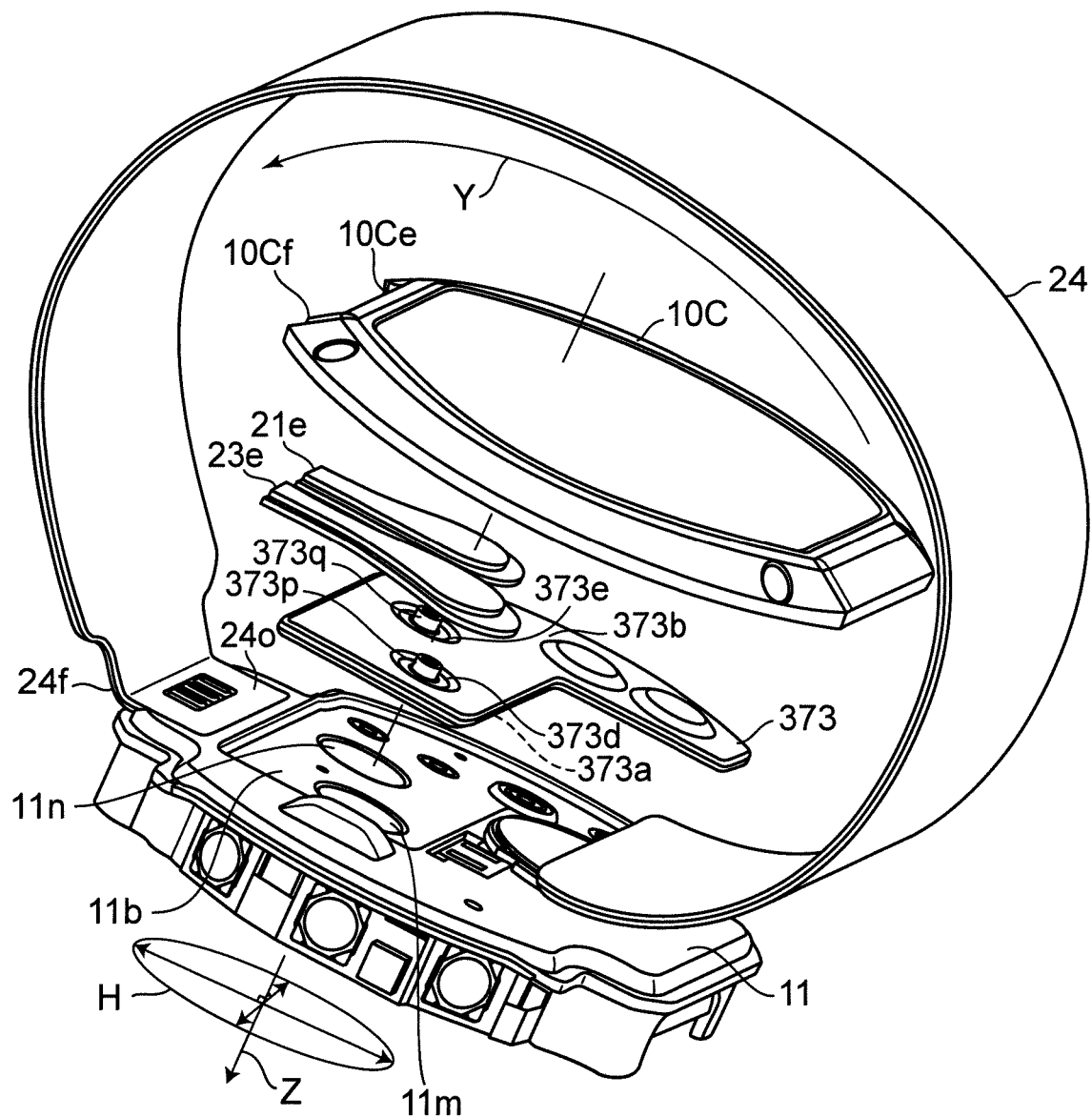
FIG. 20 is a view illustrating the back side of the main body including the curler included in the cuff structure in the disassembled state in which a back lid is removed corresponding to FIG. 7, with respect to a first modification in which the structure of the planar direction passage of the sphygmomanometer is modified.

In the first modification, as illustrated in FIG. 20, a plate-shaped member 373 made of a synthetic resin (for example, an ABS resin) is provided so as to be sandwiched between the back surface 11b of the inner case member 11 and the back lid 10C of the main body 10. In the first modification, the spacer plate 372 in FIG. 7 is omitted in order to promote the low profile of the product.

Specifically, as illustrated in FIG. 20, shallow bottomed grooves 11m, 11n having a circular pattern along the planar direction H are formed in the back surface 11b of the inner case member 11.

In an opposing surface 373a of the plate-shaped member 373 opposed to the back surface 11b of the inner case member 11, a shallow bottomed groove 373m (see FIG. 21) is formed at a position corresponding to the bottomed groove 11m. Although not illustrated, similarly a shallow bottomed groove (represented by reference numeral 373n not illustrated) is formed in a portion corresponding to the bottomed groove 11n in the opposing surface 373a of the plate-shaped member 373. When the main body 10 is assembled, in the back surface 11b of the inner case member 11 and the opposing surface 373a of the plate-shaped member 373, the portions corresponding to the surroundings of the bottomed grooves 11m, 373m are in close contact with each other to constitute a first planar direction passage 391. Although not illustrated, similarly in the back surface 11b of the inner case member 11 and the opposing surface 373a of the plate-shaped member 373, the portions corresponding to the surroundings of the bottomed grooves 11n, 373n are in close contact with each other to constitute a second planar direction passage (designated by the reference numeral 381 not illustrated). The first planar direction passage 391 communicates with the first through-hole 11c, the second through-hole 11d in FIG. 9, and the third through-hole 11g, and therefore communicates with the air discharge port 30d of the pump 30, the air intake port 31d of the first pressure sensor 31, and the inlet 33i of the On-off valve 33. The second planar direction passage 381 communicates with the second through-hole 11e and the third through-hole 11h in FIG. 9, and therefore communicates with the outlet 33e of the On-off valve 33 and the air intake port 32d of the second pressure sensor 32.

As illustrated in FIG. 20, recesses 373d, 373e having a circular pattern along the planar direction H are provided in a back surface 373b opposed to the opposing surface 373a of the plate-shaped member 373. In the centers of the recesses 373d, 373e, short cylindrical nipples 373p, 373q are formed as a second flow port piercing through the plate-shaped member 373 in the thickness direction Z, respectively. The nipples 373p, 373q communicate with the first planar direction passage 391 and the second planar direction passage 381, respectively.

Figure 23A:
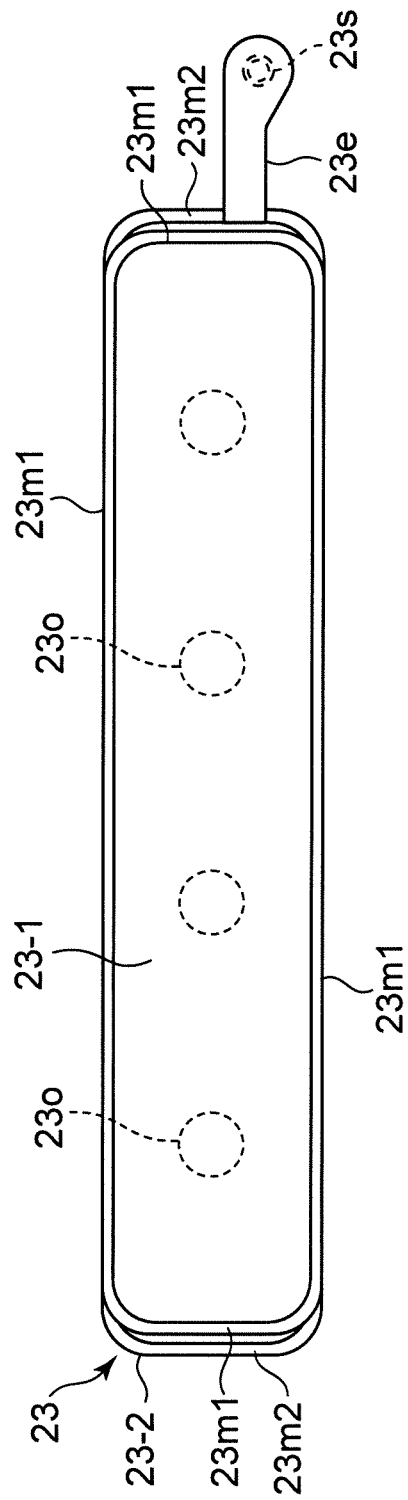
FIG. 23A is a view illustrating a planar layout of the pressing cuff included in the cuff structure.
Figure 23B:
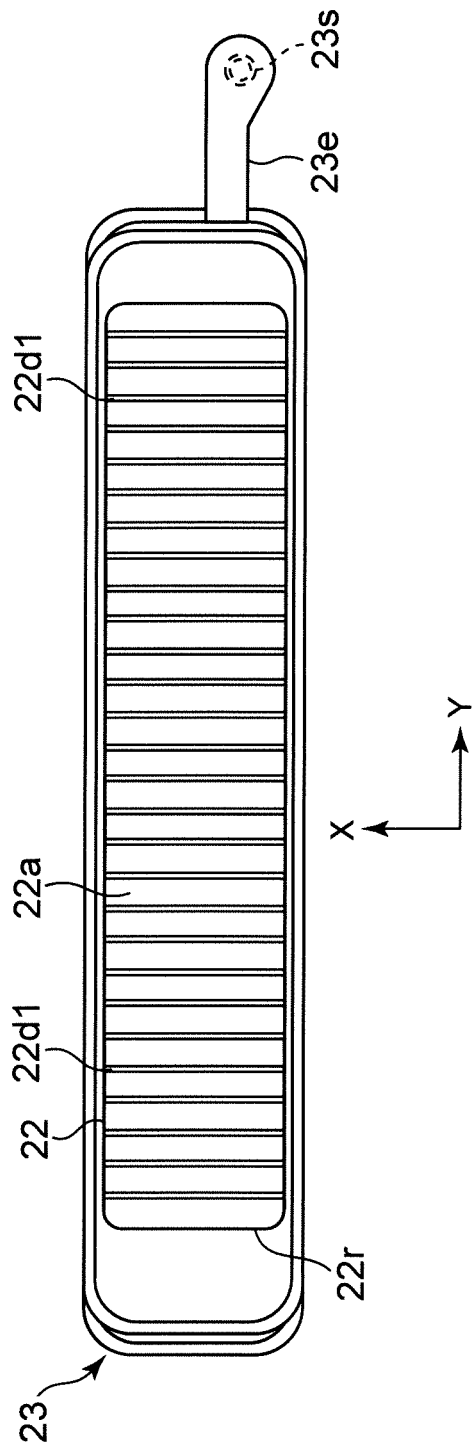
FIG. 23B is a view illustrating a planar layout of the backboard included in the cuff structure while the pressing cuff is set to a background.

FIG. 20 illustrates an extension portion 23e of the pressing cuff 23 and an extension portion 21e of the sensing cuff 21 as a second flexible passage between the back surface 373b of the plate-shaped member 373 and the back lid 10C of the main body 10. In this example, as illustrated in FIGS. 22A and 22B corresponding to FIGS. 3A and 3B, the extension portion 21e is provided at the end on the root side (+Y side) in the longitudinal direction Y of the sensing cuff 21 in order to elongate the first and second sheets 21A, 21B in a thinning manner to supply the pressure transmitting fluid (in this example, air) to the sensing cuff 21 or to discharge the pressure transmitting fluid from the sensing cuff 21. A short cylindrical portion 21s piercing through the second sheet 21B as an opposing sheet on the outer circumferential side (the side opposed to the nipple 373q) in the thickness direction is formed at the leading end (the end on the +Y side) of the extension portion 21e. As illustrated in FIGS. 23A and 23B corresponding to FIGS. 22A and 22B and FIGS. 5A and 5B, the extension portion 23e is provided at the end on the root side (+Y side) in the longitudinal direction Y of the fluid bag 23-2 on the outer circumferential side of the pressing cuff 23 in order to elongate the two sheets constituting the fluid bag 23-2 in a thinning manner to supply the pressure transmitting fluid (in this example, air) to the pressing cuff 23 or to discharge the pressure transmitting fluid from the pressing cuff 23. A short cylindrical portion 23s piercing through the opposing sheet on the outer circumferential side (the side opposed to the nipple 373p) of the fluid bag 23-2 in the thickness direction is formed at the leading end (the end on the +Y side) of the extension portion 23e.

When the cuff structure 20 including the curler 24 is attached to the main body 10, the short cylindrical portion 23s of the extension portion 23e from the pressing cuff 23 is airtightly fitted to the nipple 373p in FIG. 20, and is easy to attach. Consequently, the pressing cuff 23 is communicated with the first planar direction passage 391 (that is, the bottomed grooves 11m, 373m) through the extension portion 23e. The short cylindrical portion 21s of the extension portion 21e from the sensing cuff 21 is airtightly fitted and easily attached to the nipple 373q in FIG. 20, and is easy to attach. As a result, the sensing cuff 21 is communicated with the second planar direction passage 381 (that is, the bottomed grooves 11n, 373n) through the extension portion 21e.

Thus, during the blood pressure measurement, as illustrated by an arrow FL2 in FIG. 21, the air can be supplied from the air discharge port 30d of pump 30 to the pressing cuff 23 through first through-hole 11c, the first planar direction passage 391, and the extension portion 23e. The air can be supplied from the air discharge port 30d of the pump 30 to the sensing cuff 21 through the first through-hole 11c, the first planar direction passage 391, the On-off valve 33 in the open state, the second planar direction passage 381, and the extension portion 21e. At this point, the air is introduced from the pressing cuff 23 to the air intake port 31d of the first pressure sensor 31 through the extension portion 23e, the first planar direction passage 391, and the second through-hole 11d. The air is introduced from the sensing cuff 21 to the air intake port 32d of the second pressure sensor 32 through the extension portion 21e, the second planar direction passage 381, and the second through-hole 11e. Thus, the pressures of the pressing cuff 23 and the sensing cuff 21 are detected by the first pressure sensor 31 and the second pressure sensor 32, respectively.

In this example, the thickness of the plate-shaped member 373 in FIG. 21 is set to t4=0.7 mm, the thicknesses of the extension portions 21e, 23e are set to t5=0.6 mm, and the thickness of the back lid 10C is set to t6=0.8 mm. Thus, the thickness from the back surface 11b of the inner case member 11 to the outer surface 10Cb of the back lid 10C becomes t4+t5+t6=2.1 mm. Consequently, the low profile of the product can be achieved.

The depths of the bottomed grooves 373m, 373n and the recesses 373d, 373e in the plate-shaped member 373 are all set to 0.3 mm. As to a breakdown of the thickness t5 of the extension portion 21e, the thickness of each of the first and second sheets 21A, 21B becomes t=0.15 mm, and the thickness of a passage layer between the first and second sheets 21A, 21B becomes 0.3 mm. The breakdown of the thickness t5 of the extension portion 23e is similar to that of the thickness of the extension portion 21e.

The nipples 373p, 373q are provided in the recesses 373d, 373e, respectively, so that the dimension in which the nipples 373p, 373q protrude from the back surface 373b of the plate-shaped member 373 can be reduced in the thickness direction Z to contribute to the low profile of the product.

In the opposing surface 10Ca of the back lid 10C opposed to the back surface 11b of the inner case member 11, a recess 10Cd is provided at the positions corresponding to the nipples 373p, 373q and the short cylindrical portions 23s, 21s fitted to the nipples 373p, 373q in the planar direction H. Thus, in the pressurized state, the sheet on the inner circumferential side (the lower side in FIG. 21) of the extension portion 23e of the pressing cuff 23 and the sheet on the inner circumferential side of the extension portion 21e of the sensing cuff 21 are inflated toward the recess 10Cd. Thus, the first planar direction passage 391 and the second planar direction passage 381 can effectively be secured. Conversely, it can be said that the recess 10Cd of the back lid 10C contributes to the low profile of the product.

In the first modification, the bottomed grooves 11m, 11n are provided in both the back surface 11b of the inner case member 11 and the opposing surface 373a of the plate-shaped member 373, respectively. However, the present invention is not limited to the first modification. Alternatively, a bottomed groove may be provided in one of the back surface 11b of the inner case member 11 and the opposing surface 373a of the plate-shaped member 373 to constitute the first planar direction passage 391 and the second planar direction passage 381.

In the first modification, the inner case member 11 and the plate-shaped member 373 are different from each other. However, the present invention is not limited to the first modification. Alternatively, while including the bottomed grooves 11m, 373m and 11n, 373n, the inner case member 11 and the plate-shaped member 373 may be made of an integral member in which a material and a composition are spatially continuous. Consequently, when the main body 10 is assembled, the first planar direction passage 391 and the second planar direction passage 381 can easily be provided in the main body 10.

For example, the integral member can be formed by using a commercially available three-dimensional printer (3D printer). For example, Computer Aided Design (CAD) data representing the three-dimensional shape of the integral member is prepared and input to the 3D printer. Using the 3D printer, the integral member is formed by, for example, a powder sinter layered shaping method with nylon (polyamide) as a material. Consequently, the integral member can easily be prepared.

In the first modification, the short cylindrical nipples 373p, 373q as the second flow port are formed in the back surface 373b of the plate-shaped member 373, and the short cylindrical portions 21s, 23s are provided in the opposing sheets constituting the extension portion 21e of the sensing cuff 21 and the extension portion 23e of the pressing cuff 23 as the second flexible passage. However, the present invention is not limited to the embodiment. For example, it is assumed that the back surface 373b of the plate-shaped member 373 is formed flat while including a first opening (in this example, two openings) constituting the second flow port. It is assumed that a second opening (in this example, each one opening) penetrating through each of the opposing sheets constituting the extension portion 21e of the sensing cuff 21 and the extension portion 23e of the pressing cuff 23 as the second flexible passage in the thickness direction Z is formed in each of the opposing sheets. It is assumed that each of the opposing sheets constituting the extension portion 21e of the sensing cuff 21 and the extension portion 23e of the pressing cuff 23 is in close contact with the back surface 373b of the plate-shaped member 373 while the two second openings overlap and communicate with the two first openings. With such a configuration, during the assembly, for example, each opposing sheet adheres to the back surface 373b of the plate-shaped member 373 with an adhesive or a double-sided adhesive tape interposed therebetween, which allows the easy attachment of the second flow port and the second flexible passage. The back surface 373b of the plate-shaped member 373 is formed flat while including the first opening constituting the second flow port, and the elements (for example, the short cylindrical portions 21s, 23s) extending in the thickness direction Z are not required for the extension portion 21e of the sensing cuff 21 and the extension portion 23e of the pressing cuff 23, so that it can further contribute to the low profile of the product.

Second Modification

A second modification in which the structure of the planar direction flow passage in the main body 10 is modified will be described below. It is assumed that the disposition of the blood pressure measurement elements 30, 31, 32, 33 mounted on the surface 11a of the inner case member 11 in FIG. 8 is maintained.

Figure 24:
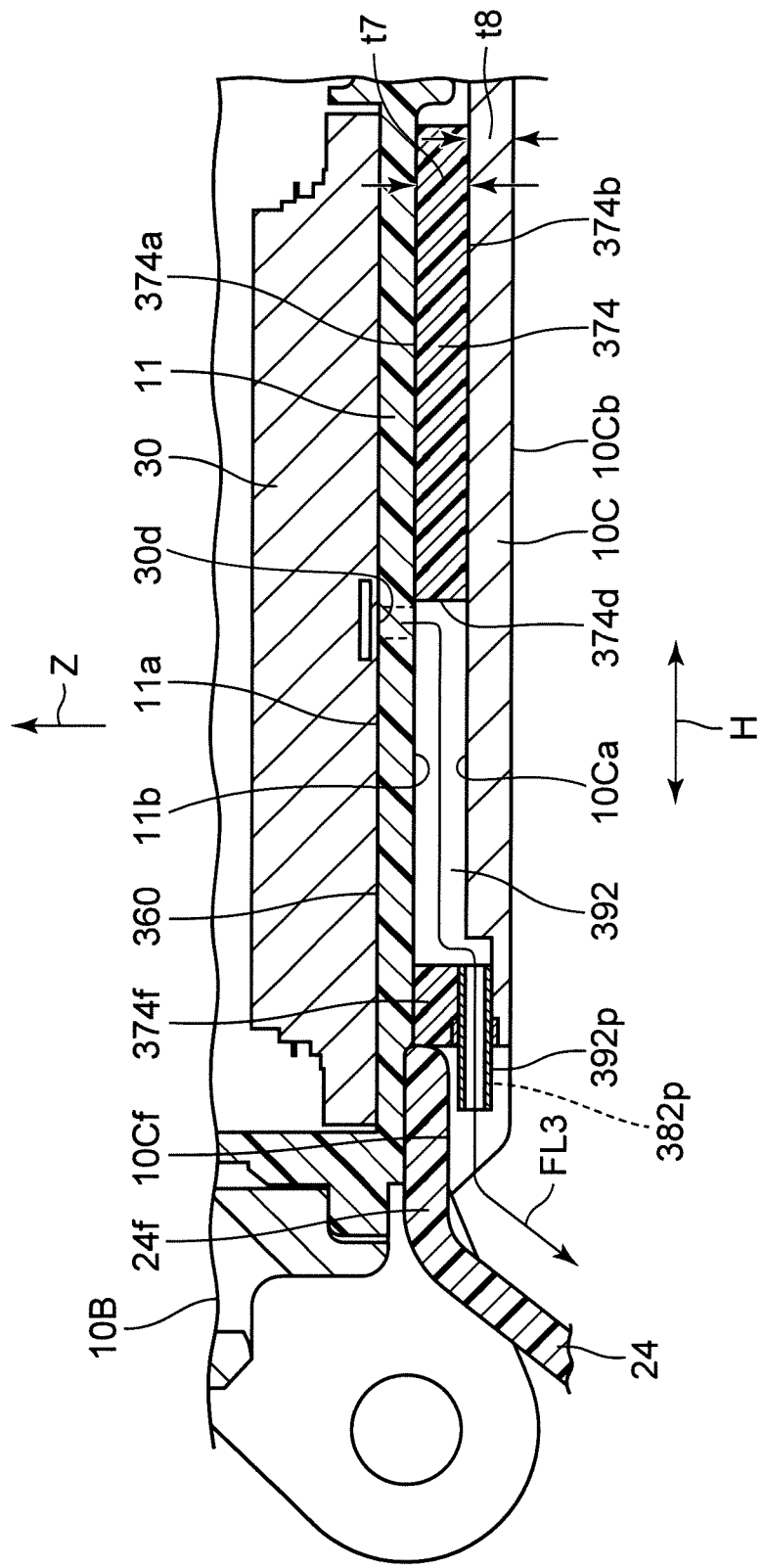
FIG. 24 is a view corresponding to FIG. 10 illustrating a sectional structure in the vicinity of the planar direction passage provided in the main body in a second modification in which the structure of the planar direction passage of the sphygmomanometer is modified.

In the second modification, as illustrated in FIG. 24 corresponding to FIG. 10, a spacer plate 374 made of a synthetic resin (for example, polyurethane) is provided so as to be sandwiched between the back surface 11b of the inner case member 11 and the back lid 10C of the main body 10. Two surfaces 374a, 374b of the spacer plate 374 are in close contact with the back surface 11b of the inner case member 11 and the opposing surface 10Ca of the back lid 10C opposed to the back surface 11b, respectively, and maintain the inner case member 11 and the plate-shaped member 371 in the state in which the inner case member 11 and the plate-shaped member 371 are separated from each other in the thickness direction Z. In order to promote the low profile of the product, the plate-shaped member 371 in FIG. 7 is made common to the back lid 10C constituting the back surface of the main body 10 in the second modification. In other words, in the second modification, the plate-shaped member 371 is constructed with the back lid 10C.

Similarly to the spacer plate 372 illustrated in FIG. 7 (and FIG. 9), the spacer plate 374 in FIG. 24 includes a pattern (constructed with an inner circumferential wall 374d) of a first planar direction passage 392 corresponding to the first planar direction passage 390 in FIG. 7 and a pattern (constructed with an inner circumferential wall 374e not illustrated) of a second planar direction passage (designated by the reference numeral 382 not illustrated) corresponding to the second planar direction passage 380 in FIG. 7.

The first planar direction passage 392 is formed between the back surface 11b of the inner case member 11 and the opposing surface 10Ca of the back lid 10C of the main body 10 in the thickness direction Z, and restricted by the inner circumferential wall 374d of the spacer plate 374 in the planar direction H. Although not illustrated, similarly the second planar direction passage 382 is formed between the back surface 11b of the inner case member 11 and the opposing surface 10Ca of the back lid 10C of the main body 10 in the thickness direction Z, and restricted by the inner circumferential wall 374e of the spacer plate 374 in the planar direction H.

In the second modification, at the circumferential edge on one side (the left side in FIG. 24) of the back lid 10C, cylindrical lateral pins 392p, 382p are provided as a third flow port that pierces through the circumferential edge in the planar direction H to protrude to the outside. The lateral pins 392p, 382p as the third flow port is oriented toward the planar direction H, which can contribute to the low profile of the product. The circumferential edge of the back lid 10C in which the lateral pins 392p, 382p are provided is hermetically sealed by a circumferential edge 374f on one side of the spacer plate 374.

The lateral pins 392p, 382p communicate with the first planar direction passage 392 and the second planar direction passage 382, respectively. During the assembly of the sphygmomanometer 1, the flexible tube 39 from the pressing cuff 23 is airtightly fitted and easily attached to the lateral pin 392p. The flexible tube 38 from the sensing cuff 21 is airtightly fitted and easily attached to the lateral pin 382p. Consequently, the pressing cuff 23 and the sensing cuff 21 are communicated with the first planar direction passage 392 and the second planar direction passage 382 through the flexible tubes 39, 38, respectively. In this example, the flexible tubes 39, 38 constitute a third flexible passage.

Thus, during the blood pressure measurement, as illustrated by an arrow FL3 in FIG. 24, the air can be supplied from the air discharge port 30d of pump 30 to the pressing cuff 23 through first through-hole 11c, the first planar direction passage 392, and flexible tube 39. The air can be supplied from the air discharge port 30d of the pump 30 to the sensing cuff 21 through the first through-hole 11c, the first planar direction passage 392, the On-off valve 33 in the open state, the second planar direction passage 382, and the flexible tube 38. At this point, the air is introduced from the pressing cuff 23 to the air intake port 31d of the first pressure sensor 31 through the flexible tube 39, the first planar direction passage 392, and the second through-hole 11d. The air is introduced from the sensing cuff 21 to the air intake port 32d of the second pressure sensor 32 through the flexible tube 38, the second planar direction passage 382, and the second through-hole 11e. Thus, the pressures of the pressing cuff 23 and the sensing cuff 21 are detected by the first pressure sensor 31 and the second pressure sensor 32, respectively.

In this example, the thickness of the spacer plate 374 in FIG. 24 is set to t7=0.8 mm, and the thickness of the back lid 10C is set to t8=0.8 mm. Thus, the thickness from the back surface 11b of the inner case member 11 to the outer surface 10Cb of the back lid 10C becomes t7+t8=1.6 mm. Consequently, the low profile of the product can be achieved.

In the above embodiment, the main body 10 includes two planar direction passages of the first planar direction passage 390 (or 391, 392) and the second planar direction passage 380 (or 381, 382). However, the present invention is not limited to the embodiment. For example, the main body 10 may include only one planar direction passage. Conversely, the main body 10 may include at least three planar direction passages.

In the embodiment, by way of example, the sensing cuff 21 is in direct contact with the left wrist 90 as the measured site. However, the present invention is not limited to the embodiment. The sensing cuff 21 may indirectly contact with the left wrist 90 with another member (for example, a cover member) interposed therebetween.

In the embodiment, the measured site on which the sphygmomanometer is worn is the left wrist 90. However, the present invention is not limited to the embodiment. The sphygmomanometer of the embodiment of the present invention may be configured so as to be optically symmetrical with respect to the sphygmomanometer 1 in FIGS. 1 and 2, and may be worn on the right wrist. The measured site may be a site except for the wrist, such as the upper arm or the leg.

In the embodiment, the main body 10 and the belt 2 are formed separately from each other, and the belt 2 is attached to the main body 10. However, the present invention is not limited to the embodiment. The main body 10 and the belt 2 may integrally be molded.

In the embodiment, the first belt 3 and the second belt 4 of the belt 2 are fastened or released by the tail lock 5. However, the present invention is not limited to the embodiment. For example, the first belt 3 and the second belt 4 may be connected to each other while a three-fold type buckle that can be opened and closed is interposed therebetween.

In the embodiment, the CPU 100 mounted on the sphygmomanometer 1 acts as the fluid storage controller, the pressurization controller, and the blood pressure calculator to perform the blood pressure measurement (the flowchart in FIG. 12). However, the present invention is not limited to the embodiment. For example, a substantial computer device, such as a smartphone, which is provided outside the sphygmomanometer 1, may act as the fluid storage controller, the pressurization controller, and the blood pressure calculator, and cause the sphygmomanometer 1 to perform the blood pressure measurement (the flowchart in FIG. 12) through the network 900.

For example, the main body of the sphygmomanometer may be configured as a table-top type separated from the cuff, and connected to the cuff (fluid bag) through a fluid-flowable tube.

The above embodiments are illustrative only, and various modifications can be made without departing from the scope of the present invention. The plurality of embodiments described above can be made independently, and the embodiments can also be combined. Although various features in different embodiments can independently be established, the features in different embodiments can also be combined.

According to a sphygmomanometer of the present embodiment, the sphygmomanometer includes a cuff to be worn while binding a measured site and a main body, wherein the main body is equipped with a substrate, a pump and a pressure sensor that are attached to one surface of the substrate, and a plate-shaped member opposed to an other surface of the substrate on an opposite side of the one surface of the substrate, the substrate includes a first through-hole at a portion corresponding to a fluid discharge port of the pump, and a second through-hole at a portion corresponding to a fluid intake port of the pressure sensor, the other surface of the substrate and an opposing surface of the plate-shaped member opposed to the other surface constitute the planar direction passage extending in a planar direction along the other surface of the substrate, the planar direction passage communicates with a fluid bag of the cuff, and the sphygmomanometer further includes:

a pressurization controller to control pressing the measured site with supplying fluid from the pump to the fluid bag through the first through-hole and the planar direction passage; and a blood pressure calculator to calculate a blood pressure based on an output of the pressure sensor while the fluid is introduced from the fluid bag to the pressure sensor through the planar direction passage and the second through-hole.

As used herein, the "planar direction passage" means a path extending in the planar direction and flowing the fluid along the extending direction.

The "fluid bag" included in the cuff has may be a single fluid bag or a plurality of fluid bags.

The "fluid" is typically air, but may be another gas or liquid.

In the sphygmomanometer of the present embodiment, while the cuff is worn while binding the measured site, the pressurization controller supplies the fluid from the fluid discharge port of the pump to the fluid bag through the first through-hole and the planar direction passage, and performs the control of pressing the measured site. At this point, the fluid is introduced from the fluid bag to the fluid intake port of the pressure sensor through the planar direction passage and the second through-hole. In this state, the blood pressure calculator calculates the blood pressure based on an output of the pressure sensor (oscillometric method).

In the sphygmomanometer, the other surface of the substrate and the opposing surface of the plate-shaped member opposed to the other surface constitute the planar direction passage extending in the planar direction along the other surface of the substrate. Thus, the low profile of the product can be achieved as compared with the case that the pump, the pressure sensor, and the fluid bag are connected by the air piping extending straight in the thickness direction as disclosed in Japanese Patent Application Publication No. 2013-220187.

Preferably the main body is integrated with the cuff. The "integrated" includes the case that the main body is integrally molded with the cuff and the case that the main body is formed separately from the cuff and integrally attached to the cuff. On the other hand, the main body may be configured as a table-top type separated from the cuff, and connected to the cuff (fluid bag) through a fluid-flowable tube.

In the sphygmomanometer of the embodiment, each of the pump and the pressure sensor has a flat outer shape along the one surface of the substrate.

In the sphygmomanometer of the embodiment, each of the pump and the pressure sensor has the flat outer shape along the one surface of the substrate. Thus, the low profile of the product can be achieved.

In the sphygmomanometer of the embodiment, the sphygmomanometer further includes a spacer plate disposed along between the substrate and the plate-shaped member to keep the substrate and the plate-shaped member in a state in which the substrate and the plate-shaped member are separated from each other in a thickness direction, wherein both surfaces of the spacer plate are in close contact with the substrate and the plate-shaped member, the spacer plate includes an inner circumferential wall making a hole penetrating through the spacer plate in the thickness direction, and the inner circumferential wall collectively surrounds the first through-hole and the second through-hole in the planar direction to form a pattern of the planar direction passage.

The sphygmomanometer of the embodiment includes the spacer plate disposed along between the substrate and the plate-shaped member to keep the substrate and the plate-shaped member in the state in which the substrate and the plate-shaped member are separated from each other in the thickness direction. Both surfaces of the spacer plate are in close contact with the substrate and the plate-shaped member. The spacer plate includes an inner circumferential wall making a hole penetrating through the spacer plate in the thickness direction. The inner circumferential wall collectively surrounds the first through-hole and the second through-hole in the planar direction to form a pattern of the planar direction passage. Thus, the planar direction passage can easily be configured while communicate with communicating with the first through-hole and the second through-hole.

In the sphygmomanometer of the embodiment, a first flow port piercing in the planar direction between the inner circumferential wall of the spacer plate and an outer circumferential wall opposed to the inner circumferential wall is provided, and the planar direction passage communicates with the fluid bag through the first flow port and a first flexible passage connected to the first flow port.

In the sphygmomanometer of the embodiment, the first flow port piercing in the planar direction between the inner circumferential wall of the spacer plate and the outer circumferential wall opposed to the inner circumferential wall is provided. The planar direction passage communicates with the fluid bag through the first flow port and the first flexible passage connected to the first flow port. Consequently, the fluid can be supplied from the pump to the fluid bag through the first through-hole, the planar direction passage, the first flow port, and the first flexible passage. The fluid can be introduced from the fluid bag to the pressure sensor through the first flexible passage, the first flow port, the planar direction passage, and the second through-hole. The first flow port is oriented toward the planar direction, which can contribute to the low profile of the product.

In the sphygmomanometer of the embodiment, the first flow port includes a cylindrical lateral pin protruding from the outer circumferential wall of the spacer plate along the planar direction, and a flexible tube constituting the first flexible passage is fitted and attached to the lateral pin.

In the sphygmomanometer of the embodiment, the first flow port includes the cylindrical lateral pin protruding from the spacer plate along the planar direction, and the flexible tube constituting the first flexible passage is fitted and attached to the lateral pin. Thus, during the assembly, the first flow port and the flexible tube constituting the first flexible passage can easily be attached to each other.

In the sphygmomanometer of the embodiment, a bottomed groove extending along the planar direction is formed on one or both of the other surface of the substrate and the opposing surface of the plate-shaped member, the bottomed groove communicates in common with the first through-hole and the second through-hole, and portions corresponding to a surrounding of the bottomed groove in the other surface of the substrate and the opposing surface of the plate-shaped member are in close contact with each other, whereby the bottomed groove constitutes the planar direction passage.

As used herein, the "bottomed groove" means a groove including a bottom in the substrate or the plate-shaped member in which the groove is formed. The "bottomed groove" does not include a slit or the like penetrating through the substrate or the plate-shaped member in the thickness direction.

In the sphygmomanometer of the embodiment, the bottomed groove extending along the planar direction is formed on one or both of the other surface of the substrate and the opposing surface of the plate-shaped member. The bottomed groove communicates in common with the first through-hole and the second through-hole, and portions corresponding to a surrounding of the bottomed groove in the other surface of the substrate and the opposing surface of the plate-shaped member are in close contact with each other. Consequently, the bottomed groove constitutes the planar direction passage. Thus, the planar direction passage can easily be configured while communicate with communicating with the first through-hole and the second through-hole.

In the sphygmomanometer of the embodiment, a second flow port piercing through the plate-shaped member in the thickness direction is provided in the plate-shaped member, and the planar direction passage communicates with the fluid bag through the second flow port and a second flexible passage connected to the second flow port.

In the sphygmomanometer of the embodiment, the second flow port piercing through the plate-shaped member in the thickness direction is provided in the plate-shaped member. The planar direction passage communicates with the fluid bag through the second flow port and a second flexible passage connected to the second flow port. Consequently, the fluid can be supplied from the pump to the fluid bag through the first through-hole, the planar direction passage, the second flow port, and the second flexible passage. The fluid can be introduced from the fluid bag to the pressure sensor through the second flexible passage, the second flow port, the planar direction passage, and the second through-hole.

In the sphygmomanometer of the embodiment, a recess is provided on a back surface on an opposite side of the opposing surface of the plate-shaped member, a short cylindrical nipple constituting the second flow port is formed in the recess, the second flexible passage is formed into a bag shape by bringing circumferential edges of two elongated sheets into close contact with each other, the second flexible passage includes a fluid-flowable short cylindrical portion formed by piercing through an opposing sheet on a side opposed to the nipple in the two sheets in the thickness direction, and the short cylindrical portion is fitted and attached to the nipple.

In the sphygmomanometer of the embodiment, the short cylindrical nipple constituting the second flow port is formed in the recess provided on the back surface on the opposite side of the opposing surface of the plate-shaped member. The second flexible passage is formed into a bag shape by bringing circumferential edges of two elongated sheets into close contact with each other, and the second flexible passage includes a fluid-flowable short cylindrical portion formed by piercing through an opposing sheet on a side opposed to the nipple in the two sheets in the thickness direction. The short cylindrical portion is fitted and attached to the nipple. Thus, during the assembly, the second flow port and the second flexible passage can easily be attached to each other. The nipple is provided in the recess, so that the dimension in which the nipple protrudes from the back surface of the plate-shape member can be reduced in the thickness direction to contribute to the low profile of the product.

In the sphygmomanometer of the embodiment, a back surface on the opposite side of the opposing surface of the plate-shaped member is formed flat while including a first opening constituting the second flow port, the second flexible passage is formed into a bag shape by bringing the circumferential edges of two elongated sheets into close contact with each other, the second flexible passage includes a second opening formed by piercing through an opposing sheet on the side opposed to the opposing surface of the plate-shaped member in the two sheets in the thickness direction, and the opposing sheet is in close contact with the back surface of the plate-shaped member while the second opening overlaps and communicates with the first opening.

In the sphygmomanometer of the embodiment, the back surface on the opposite side of the opposing surface of the plate-shaped member is formed flat while including the first opening constituting the second flow port. The second flexible passage is formed into the bag shape by bringing the circumferential edges of two elongated sheets into close contact with each other, and the second flexible passage includes the opening formed by piercing through the opposing sheet on the side opposed to the opposing surface of the plate-shaped member in the two sheets in the thickness direction. The opposing sheet is in close contact with the back surface of the plate-shaped member while the second opening overlaps and communicates with the first opening. Thus, during the assembly, for example, the opposing sheet adheres to the back surface of the plate-shaped member with an adhesive or a double-sided adhesive tape interposed therebetween, which allows the easy attachment of the second flow port and the second flexible passage. The back surface on the opposite side of the opposing surface of the plate-shaped member is formed flat while including the first opening constituting the second flow port, and the element (for example, the short cylindrical portion) extending in the thickness direction is not required for the second flexible passage, so that it can further contribute to the low profile of the product.

In the sphygmomanometer of the embodiment, the substrate and the plate-shaped member are made of an integral member in which a material and a composition are spatially continuous while including the bottomed groove.

As used herein, the "integral member in which the material and the composition are spatially continuous" can be formed using, for example, a commercially available three-dimensional printer (3D printer). In the case that the substrate and the plate-shaped member are integrated with each other by welding or adhesion, because a welded place or a adhesion place becomes spatially discontinuous with another place with respect to the material or the composition, the case is not included in the "integral member in which the material and the composition are spatially continuous".

In the sphygmomanometer of the embodiment, the substrate and the plate-shaped member are made of the integral member in which a material and a composition are spatially continuous while including the bottomed groove. Thus, during the assembly, the planar direction passage can easily be provided in the main body.

In the sphygmomanometer of the embodiment, the plate-shaped member is constructed with a back lid constituting a back surface of the main body.

In the sphygmomanometer of the embodiment, the plate-shaped member is constructed with a back lid constituting the back surface of the main body. Thus, the low profile of the product can further be attained as compared with the case that the plate-shaped member is provided separately from the back lid. The sphygmomanometer can easily be configured without increasing the number of components.

In the sphygmomanometer of the embodiment, a third flow port piercing through a circumferential edge of the back lid in the planar direction is provided at the circumferential edge, and the planar direction passage communicates with the fluid bag through the third flow port and a third flexible flow passage connected to the third flow port.

In the sphygmomanometer of the embodiment, the third flow port piercing through the circumferential edge of the back lid in the planar direction is provided at the circumferential edge. The planar direction passage communicates with the fluid bag through the third flow port and a third flexible flow passage connected to the third flow port. Consequently, the fluid can be supplied from the pump to the fluid bag through the first through-hole, the planar direction passage, the third flow port, and the third flexible passage. The fluid can be introduced from the fluid bag to the pressure sensor through the third flexible passage, the third flow port, the planar direction passage, and the second through-hole. The third flow port is oriented toward the planar direction, which can contribute to the low profile of the product.

In the sphygmomanometer of the embodiment, the third flow port includes a cylindrical lateral pin protruding outward from the back lid along the planar direction, and a flexible tube constituting the third flexible passage is fitted and attached to the lateral pin.

In the sphygmomanometer of the embodiment, the third flow port includes the cylindrical lateral pin protruding outward from the back lid along the planar direction, and the flexible tube constituting the third flexible passage is fitted and attached to the lateral pin. Thus, during the assembly, the third flow port and the flexible tube constituting the third flexible passage can easily be attached to each other.

In the sphygmomanometer of the embodiment, the fluid intake port is provided in an abutting surface of the pressure sensor while the fluid discharge port is provided in an abutting surface of the pump abutting on the one surface of the substrate, and a sealing unit that fluid-tightly attaches the pump and the pressure sensor to the one surface of the substrate is provided between the one surface of the substrate and the abutting surface around the fluid discharge port of the pump and the abutting surface around the fluid intake port of the pressure sensor.

As used herein, the "fluid-tight" means either air-tight or liquid-tight.

In the sphygmomanometer of the embodiment, the fluid intake port is provided in the abutting surface of the pressure sensor while the fluid discharge port is provided in the abutting surface of the pump abutting on the one surface of the substrate. Thus, the pump can deliver the fluid to the planar direction passage through the fluid discharge port provided in the abutting surface of the pump and the first through-hole. The pressure sensor can introduce the fluid from the planar direction passage through the second through-hole and the fluid intake port provided in the abutting surface of the pressure sensor. The sealing unit that fluid-tightly attaches the pump and the pressure sensor to the one surface of the substrate is provided between the one surface of the substrate and the abutting surface around the fluid discharge port of the pump and the abutting surface around the fluid intake port of the pressure sensor. Thus, the fluid is prevented from leaking between the one surface of the substrate and the abutting surfaces of the pump and the pressure sensor.

In the sphygmomanometer of the embodiment, the plate-shaped member includes a layer made of stainless steel or another metal.

In the sphygmomanometer of the embodiment, the plate-shaped member includes a layer made of stainless steel or another metal, so that mechanical strength of the plate-shaped member is enhanced. Thus, the thickness of the plate-shaped member can be set thinner as compared with the case that the plate-shaped member is made of only a general synthetic resin material. As a result, the low profile of the product can further be achieved.

In the sphygmomanometer of the embodiment, the cuff includes a belt that extends from the main body and is worn while binding the measured site, and cuff structure having a belt-shape and being disposed opposite to an inner circumferential surface of the belt, one end of the cuff structure being attached to the main body, and the cuff structure includes pressing cuff having a bag-shape, extending along a longitudinal direction of the cuff structure, and being one of the fluid bags, such that the pressing cuff receives supply of a pressurization fluid to press the measured site, a sensing cuff having a bag-shape to store a pressure transmitting fluid, being disposed along an inner circumferential surface of the pressing cuff, extending in the longitudinal direction so as to cross an artery passage portion of the measured site, and being one of the fluid bags, and a backboard interposed between the pressing cuff and the sensing cuff and extending along the longitudinal direction to transmit pressing force from the pressing cuff to the sensing cuff.

As used herein, in the "belt" that "extends from the main body", the main body and the belt may be integrally molded, or the main body and the belt may be formed separately from each other and the belt may be attached to the main body. As to the belt itself, the first belt extending on one side in one direction from the main body and the second belt extending on the other direction from the main body may be fastened or released by the tail lock, or coupled together by a buckle that can be opened and closed. The "inner circumferential surface" of the belt means a surface that becomes the inner circumferential side in the mounted state binding the measured site. Similarly, the "inner circumferential surface" of the pressing cuff means the surface that becomes the inner circumferential side in the mounted state binding the measured site.

The "pressure transmitting fluid" may be stored in the sensing cuff at the manufacturing stage of the sphygmomanometer, or stored in and discharged from the sensing cuff each time the blood pressure is measured.

The "longitudinal direction" of the cuff structure corresponds to the circumferential direction of the measured site in the mounted state binding the measured site.

In the sphygmomanometer of the embodiment, the belt extending from the main body binds the measurement site, and the belt-shaped cuff structure in which one end attached to the main body is worn on the measured site while disposed on the inner circumferential side closer to the measured site than the belt. In the worn state, the bag-shaped pressing cuff included in the cuff structure extends along the circumferential direction of the measured site. The bag-shaped sensing cuff included in the cuff structure is disposed on the inner circumferential side with respect to the pressing cuff, and extends in the circumferential direction so as to cross the artery passage portion of the measured site. The backboard included in the cuff structure is interposed between the pressing cuff and the sensing cuff, and extends along the circumferential direction of the measured site.

During the blood pressure measurement, for example, the pressure transmitting fluid is stored in the sensing cuff. In that state, the pressurization controller performs the control of pressing the measured site by supplying the pressurization fluid from the pump mounted on the main body to the pressing cuff. At this point, the backboard transmits the pressing force from the pressing cuff to the sensing cuff. The sensing cuff presses the measured site (including the artery passage portion). During a pressurization process or a decompression process of the pressing cuff, the blood pressure calculator calculates the blood pressure based on the pressure of the pressure transmitting fluid stored in the sensing cuff (oscillometric method).

In the sphygmomanometer, the sensing cuff detects the pressure itself applied to the artery passage portion of the measured site. Thus, as a result of setting of a smaller dimension (for example, about 25 mm) in the width direction of the belt and the cuff structure (that is, the cuff), the blood pressure can accurately be measured even if the pressing cuff is largely inflated in the thickness direction to generate a compression loss during the pressurization. In the worn state, the sensing cuff extends in the circumferential direction so as to cross the artery passage portion of the measured site. Thus, when the user actually wears the sphygmomanometer on the measured site, even if the cuff is displaced to some extent in the circumferential direction of the measured site along with the main body, the sensing cuff does not come off from the artery passage portion of the measured site. Thus, the blood pressure measurement value can be prevented from varying with respect to the actual blood pressure, and resultantly the blood pressure can accurately be measured.

Because the cuff structure is not attached to the belt, the dimension in the longitudinal direction (corresponding to the circumferential direction of the measured site) of the cuff structure can be set to the optimum size regardless of the belt.

Desirably the belt has flexibility in the thickness direction of the belt, and is made of a material exhibiting substantially non-stretchability in the longitudinal direction (corresponding to the circumferential direction of the measured site) of the belt. Consequently, the belt can easily bind and restrain the outer circumferential side of the cuff structure during the wear, and assist compression of the measured site during the blood pressure measurement.

According to another aspect of the present embodiment, a device includes a cuff to be worn while binding a measured site, and a main body including a blood pressure measurement element, wherein the main body is equipped with a substrate, a pump and a pressure sensor that are attached to one surface of the substrate as the blood pressure measurement element, and a plate-shaped member opposed to the other surface of the substrate on an opposite side of the one surface of the substrate, the substrate includes the first through-hole at a portion corresponding to a fluid discharge port of the pump, and the second through-hole at a portion corresponding to a fluid intake port of the pressure sensor, the other surface of the substrate and an opposing surface of the plate-shaped member opposed to the other surface constitute the planar direction passage extending in a planar direction along the other surface of the substrate, the planar direction passage communicates with a fluid bag of the cuff, and the device further includes a pressurization controller to control pressing the measured site with supplying fluid from the pump to the fluid bag through the first through-hole and the planar direction passage, and a blood pressure calculator to calculate a blood pressure based on an output of the pressure sensor while the fluid is introduced from the fluid bag to the pressure sensor through the planar direction passage and the second through-hole.

The "device" of the present disclosure broadly includes a device having a blood pressure measurement function, and may be configured as a wristwatch type wearable device such as a smart watch.

In the device of the present embodiment, the other surface of the substrate and the opposing surface opposed to the other surface of the plate-shaped member constitute the planar direction passage along the substrate. Thus, the low profile of the product can be achieved.

According to yet another aspect of the present embodiment, a blood pressure measurement method for measuring a blood pressure of a measured site using a sphygmomanometer including a cuff that is worn while binding the measured site and a main body which is equipped with a substrate, a pump and a pressure sensor that are attached to one surface of the substrate, and a plate-shaped member opposed to an other surface of the substrate on an opposite side of the one surface of the substrate, the substrate including a first through-hole at a portion corresponding to a fluid discharge port of the pump and a second through-hole at a portion corresponding to a fluid intake port of the pressure sensor, the other surface of the substrate and an opposing surface of the plate-shaped member opposed to the other surface constituting a planar direction passage extending in a planar direction along the other surface of the substrate, and the planar direction passage communicating with a fluid bag of the cuff, the blood pressure measurement method includes, while the cuff is worn on the measured site, controlling pressing the measured site with supplying fluid from the pump to the fluid bag through the first through-hole and the planar direction passage, and calculating a blood pressure based on an output of the pressure sensor while the fluid is introduced from the fluid bag to the pressure sensor through the planar direction passage and the second through-hole.

In the blood pressure measurement method of the embodiment, when the cuff is worn while binding the measured site, the fluid is supplied from the fluid discharge port of the pump to the fluid bag through the first through-hole and the planar direction passage to perform the control to press the measured site. At this point, the fluid is introduced from the fluid bag to the fluid intake port of the pressure sensor through the planar direction passage and the second through-hole. In this state, the blood pressure is calculated based on the output of the pressure sensor. In the blood pressure measurement method, the fluid can successfully be supplied from the pump to the fluid bag, and the fluid pressure can successfully be transmitted from the fluid bag to the pressure sensor.

As apparent from the above, the low profile of the product can be achieved in the sphygmomanometer and the device of the present embodiment. In the blood pressure measurement method, the fluid can successfully be supplied from the pump to the fluid bag, and the fluid pressure can successfully be transmitted from the fluid bag to the pressure sensor.

The above embodiments are illustrative, and are modifiable in a variety of ways without departing from the scope of this invention. It is to be noted that the various embodiments described above can be appreciated individually within each embodiment, but the embodiments can be combined together. It is also to be noted that the various features in different embodiments can be appreciated individually by its own, but the features in different embodiments can be combined.

What is claimed is:

1. A sphygmomanometer comprising:

a cuff configured to be worn and bound at a measured site; and a main body, wherein the main body is equipped with a substrate, a pump and a pressure sensor are housed within the main body and are attached to one surface of the substrate, a plate-shaped member opposed to an other surface of the substrate on an opposite side of the one surface of the substrate is also housed within the main body, the substrate includes a first through-hole at a portion corresponding to a fluid discharge port of the pump, and a second through-hole at a portion corresponding to a fluid intake port of the pressure sensor, the other surface of the substrate and an opposing surface of the plate-shaped member opposed to the other surface constitute a planar direction passage extending in a planar direction along the other surface of the substrate, the planar direction passage communicates with a fluid bag of the cuff, and the sphygmomanometer further comprises:

a pressurization controller to control pressing the measured site by supplying fluid from the pump to the fluid bag through the first through-hole and the planar direction passage; and a blood pressure calculator to calculate a blood pressure based on an output of the pressure sensor while the fluid is introduced from the fluid bag to the pressure sensor through the planar direction passage and the second through-hole.

2. The sphygmomanometer according to claim 1, wherein each of the pump and the pressure sensor includes a flat outer shape portion along the one surface of the substrate.

3. The sphygmomanometer according to claim 1, further comprising a spacer plate disposed between the substrate and the plate-shaped member to keep the substrate and the plate-shaped member in a state in which the substrate and the plate-shaped member are separated from each other in a thickness direction,
wherein a first surface of the spacer plate is in contact with the substrate, and a second surface of the spacer plate is in contact with the plate-shaped member,
the spacer plate includes an inner circumferential wall making a hole penetrating through the spacer plate in the thickness direction, and
the inner circumferential wall surrounds the first through-hole and the second through-hole in the planar direction to form a pattern of the planar direction passage.

4. The sphygmomanometer according to claim 3, wherein the spacer plate includes an outer circumferential wall opposed to the inner circumferential wall, and
a first flow port piercing in the planar direction between the inner circumferential wall of the spacer plate and the outer circumferential wall is provided on the spacer plate, and
the planar direction passage communicates with the fluid bag through the first flow port and a first flexible passage connected to the first flow port.

5. The sphygmomanometer according to claim 4, wherein the first flow port includes a cylindrical lateral pin protruding from the outer circumferential wall along the planar direction, and
a flexible tube constituting the first flexible passage is fitted and attached to the lateral pin.

6. The sphygmomanometer according to claim 1, wherein a groove extending along the planar direction is formed on one or both of the other surface of the substrate and the opposing surface of the plate-shaped member,
the groove communicates with the first through-hole and the second through-hole, and portions corresponding to a surrounding of the groove in the other surface of the substrate and the opposing surface of the plate-shaped member are in contact with each other, whereby the groove constitutes the planar direction passage.

7. The sphygmomanometer according to claim 6, wherein a flow port piercing through the plate-shaped member in a thickness direction is provided in the plate-shaped member, and
the planar direction passage communicates with the fluid bag of the cuff through the flow port and a flexible passage connected to the flow port.

8. The sphygmomanometer according to claim 7, wherein a recess is provided on a back surface on an opposite side of the opposing surface of the plate-shaped member,
a cylindrical nipple constituting the flow port is formed in the recess of the plate-shaped member,
the flexible passage forms an enclosure by circumferential edges of two elongated sheets being in contact with each other,
the flexible passage includes a fluid-passable cylindrical portion that pierces through one of the two elongated sheets that is on a side opposed to the nipple in the thickness direction, and
the cylindrical portion is fitted and attached to the nipple.

9. The sphygmomanometer according to claim 7, wherein a back surface on an opposite side of the opposing surface of the plate-shaped member is flat and includes a first opening constituting the flow port,
the flexible passage is forms an enclosure by circumferential edges of two elongated sheets being in contact with each other,
the flexible passage includes a second opening that pierces through one of the two elongated sheets on the side opposed to the opposing surface of the plate-shaped member in the thickness direction, and
the one of the two elongated sheets is in contact with the back surface of the plate-shaped member and the second opening overlaps and communicates with the first opening.

10. The sphygmomanometer according to claim 6, wherein the substrate and the plate-shaped member are made of an integral member in which a material and a composition are spatially continuous.

11. The sphygmomanometer according to claim 1, wherein the plate-shaped member is constructed with a back lid constituting a back surface of the main body.

12. The sphygmomanometer according to claim 11, wherein a flow port piercing through a circumferential edge of the back lid in the planar direction is provided at the circumferential edge, and
the planar direction passage communicates with the fluid bag through the flow port and a flexible flow passage connected to the flow port.

13. The sphygmomanometer according to claim 12, wherein the flow port includes a cylindrical lateral pin protruding outward from the back lid along the planar direction, and
a flexible tube constituting the flexible passage is fitted and attached to the lateral pin.

14. The sphygmomanometer according to claim 1, wherein
the fluid intake port is provided on a connecting surface of the pressure sensor connecting to the one surface of the substrate, and the fluid discharge port is provided on a connecting surface of the pump connecting to the one surface of the substrate, and
a sealing unit that fluid-tightly attaches the pump and the pressure sensor to the one surface of the substrate is provided between the one surface of the substrate and the connecting surface around the fluid discharge port of the pump and the connecting surface around the fluid intake port of the pressure sensor.

15. The sphygmomanometer according to claim 1, wherein the plate-shaped member includes a layer made of stainless steel or another metal.

16. The sphygmomanometer according to claim 1, wherein the cuff includes:
a belt that extends from the main body and is configured to be worn at the measured site; and
a cuff structure that forms a belt-shape and is disposed opposite to an inner circumferential surface of the belt, one end of the cuff structure being attached to the main body, and
the cuff structure includes:
a pressing cuff that forms an enclosure, and extends along a longitudinal direction of the cuff structure, such that the pressing cuff receives supply of a pressurization fluid to press the measured site;
a sensing cuff that forms an enclosure to store a pressure transmitting fluid, is disposed along an inner circumferential surface of the pressing cuff, and extends in the longitudinal direction so as to cross an artery passage portion of the measured site; and a backboard interposed between the pressing cuff and the sensing cuff and extending along the longitudinal direction to transmit pressing force from the pressing cuff to the sensing cuff, and wherein the fluid bag of the cuff is one of two fluid bags, and the two fluid bags are formed by the enclosure of the pressing cuff and the enclosure of the sensing cuff.

17. A device comprising:

a cuff configured to be worn and bound at a measured site; and a main body including a blood pressure measurement element, wherein the main body is equipped with a substrate, a pump and a pressure sensor are housed within the main body and are attached to one surface of the substrate as the blood pressure measurement element, a plate-shaped member opposed to an other surface of the substrate on an opposite side of the one surface of the substrate is also housed within the main body, the substrate includes a first through-hole at a portion corresponding to a fluid discharge port of the pump, and a second through-hole at a portion corresponding to a fluid intake port of the pressure sensor, the other surface of the substrate and an opposing surface of the plate-shaped member opposed to the other surface constitute a planar direction passage extending in a planar direction along the other surface of the substrate, the planar direction passage communicates with a fluid bag of the cuff, and the device further comprises:

a pressurization controller to control pressing the measured site with supplying fluid from the pump to the fluid bag through the first through-hole and the planar direction passage; and a blood pressure calculator to calculate a blood pressure based on an output of the pressure sensor while the fluid is introduced from the fluid bag to the pressure sensor through the planar direction passage and the second through-hole.

18. A blood pressure measurement method for measuring a blood pressure of a measured site using a sphygmomanometer including a cuff configured to be worn and bound to the measured site and a main body which is equipped with a substrate, a pump and a pressure sensor that are housed within the main body and are attached to one surface of the substrate, and a plate-shaped member opposed to an other surface of the substrate on an opposite side of the one surface of the substrate that is also housed within the main body, the substrate including a first through-hole at a portion corresponding to a fluid discharge port of the pump and a second through-hole at a portion corresponding to a fluid intake port of the pressure sensor, the other surface of the substrate and an opposing surface of the plate-shaped member opposed to the other surface constituting a planar direction passage extending in a planar direction along the other surface of the substrate, and the planar direction passage communicating with a fluid bag of the cuff, the blood pressure measurement method comprising:

applying the cuff to be worn on the measured site;

controlling pressing the measured site with supplying fluid from the pump to the fluid bag through the first through-hole and the planar direction passage; and calculating a blood pressure based on an output of the pressure sensor while introducing the fluid from the fluid bag to the pressure sensor through the planar direction passage and the second through-hole.

* * * * *